US008497294B2

(12) United States Patent
Woodhead et al.

(10) Patent No.: US 8,497,294 B2
(45) Date of Patent: Jul. 30, 2013

(54) COMPOSITIONS COMPRISING (S)-2-AMINO-1-(4-CHLOROPHENYL)-1-[4-(1H-PYRAZOL-4-YL)-PHENYL]-ETHANOL AS MODULATOR OF PROTEIN KINASES

(75) Inventors: Steven John Woodhead, San Diego, CA (US); David Charles Rees, Cambridge (GB); Kyla Merriom Grimshaw, Cambridge (GB)

(73) Assignees: Astex Therapeutics Limited, Cambridge (GB); The Institute of Cancer Research: Royal Cancer Hospital, London (GB); Cancer Research Technology Limtied, London (GB)

(*) Notice: Subject to any disclaimer, the term of this patent is extended or adjusted under 35 U.S.C. 154(b) by 0 days.

(21) Appl. No.: 13/180,127

(22) Filed: Jul. 11, 2011

(65) Prior Publication Data

US 2011/0269808 A1 Nov. 3, 2011

Related U.S. Application Data

(63) Continuation of application No. 12/531,013, filed as application No. PCT/GB2008/050180 on Mar. 14, 2008, now abandoned.

(60) Provisional application No. 60/894,752, filed on Mar. 14, 2007.

(30) Foreign Application Priority Data

Mar. 14, 2007 (GB) .................................. 0704932.3

(51) Int. Cl.
*A61K 31/415* (2006.01)
*C07D 231/12* (2006.01)

(52) U.S. Cl.
USPC ........................................ 514/406; 548/375.1

(58) Field of Classification Search
USPC ........................................ 514/406; 548/375.1
See application file for complete search history.

(56) References Cited

U.S. PATENT DOCUMENTS

| | | | |
|---|---|---|---|
| 5,532,356 A | 7/1996 | Smyser et al. |
| 5,922,744 A | 7/1999 | Harrison et al. |
| 6,010,837 A | 1/2000 | Clark et al. |
| 6,015,825 A | 1/2000 | Bell et al. |
| 6,020,357 A | 2/2000 | Pinto et al. |
| 6,200,978 B1 | 3/2001 | Maw et al. |
| 7,393,842 B2 | 7/2008 | Makriyannis et al. |
| 7,799,782 B2 | 9/2010 | Munson et al. |
| 8,247,576 B2 | 8/2012 | Berdini et al. |
| 8,343,953 B2 | 1/2013 | Davies et al. |
| 2002/0091116 A1 | 7/2002 | Zhu et al. |
| 2004/0122230 A1 | 6/2004 | Welsh et al. |
| 2005/0261315 A1 | 11/2005 | Mehta et al. |
| 2010/0166699 A1 | 7/2010 | Thompson et al. |
| 2011/0144080 A1 | 6/2011 | Berdini et al. |
| 2013/0005702 A1 | 1/2013 | Berdini et al. |

FOREIGN PATENT DOCUMENTS

| | | |
|---|---|---|
| EP | 1024138 A1 | 8/2000 |
| GB | 2427406 A | 12/2006 |
| JP | 2000-016984 A | 1/2000 |
| WO | 90/09381 A1 | 8/1990 |
| WO | 91/11445 A1 | 8/1991 |
| WO | 94/29300 A1 | 12/1994 |
| WO | 95/10513 A1 | 4/1995 |
| WO | 97/01552 A1 | 1/1997 |
| WO | 97/36886 A1 | 10/1997 |
| WO | 98/04528 A2 | 2/1998 |
| WO | 98/25617 A1 | 6/1998 |
| WO | 99/38508 A1 | 8/1999 |
| WO | 00/07996 A2 | 2/2000 |
| WO | 00/14066 A1 | 3/2000 |
| WO | 00/31063 A1 | 6/2000 |
| WO | 00/39091 A1 | 7/2000 |
| WO | 00/66562 A1 | 11/2000 |
| WO | 00/69859 A1 | 11/2000 |
| WO | 01/19788 A2 | 3/2001 |
| WO | 01/19798 A2 | 3/2001 |
| WO | 01/32653 A1 | 5/2001 |
| WO | 01/64642 A2 | 9/2001 |
| WO | 01/91754 A1 | 12/2001 |
| WO | 02/088090 A2 | 11/2002 |
| WO | 03/011855 A2 | 2/2003 |
| WO | 03/028686 A1 | 4/2003 |
| WO | 03/030898 A1 | 4/2003 |
| WO | 03/048081 A2 | 6/2003 |
| WO | 03/048158 A1 | 6/2003 |
| WO | 03/059884 A1 | 7/2003 |

(Continued)

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
Taylor, S.S. et al., PKA: a portrait of protein kinase dynamics, Biochemica et Biophysica, 1697, 2004, pp. 259-269.
Hill, Michelle M. et al., Inhibition of protein kinase B/Akt: implications for cancer therapy, Pharmacology & Therapeutics, 93, 2002, pp. 243-251.
Barnett, Stanley F. et al., The Akt/PKB Family of Protein Kinases: A Review of Small Molecule Inhibitors and Progress Towards Target Validation, Current Topics in Medicinal Chemistry, 5, 2005, pp. 109-125.

(Continued)

*Primary Examiner* — Shawquia Young
(74) *Attorney, Agent, or Firm* — Heslin Rothenberg Farley & Mesiti P.C.

(57) ABSTRACT

The invention provides a composition comprising (S)2-amino-1-(4-chloro-phenyl)-1-[4-(1H-pyrazol-4-yl)-phenyl]-ethanol, wherein the composition is either substantially free of (R)2-amino-1-(4-chloro-phenyl)-1-[4-(1H-pyrazol-4-yl)-phenyl]-ethanol or the composition contains a mixture of the (S) and (R) enantiomers in which the (S) enantiomer predominates. Also provided are processes for the preparation of the (S)2-amino-1-(4-chloro-phenyl)-1-[4-(1H-pyrazol-4-yl)-phenyl]-ethanol, novel process intermediates and methods for making the novel process intermediates.

8 Claims, No Drawings

FOREIGN PATENT DOCUMENTS

| | | |
|---|---|---|
| WO | 03/068230 A1 | 8/2003 |
| WO | 03/080545 A2 | 10/2003 |
| WO | 03/086247 A1 | 10/2003 |
| WO | 03/090680 A2 | 11/2003 |
| WO | 2004/011460 A2 | 2/2004 |
| WO | 2004/110350 A2 | 12/2004 |
| WO | 2005/003101 A2 | 1/2005 |
| WO | 2005/012256 A1 | 2/2005 |
| WO | 2005/035506 A1 | 4/2005 |
| WO | 2005/061460 A1 | 7/2005 |
| WO | 2005/061463 A1 | 7/2005 |
| WO | 2005/117909 A2 | 12/2005 |
| WO | 2006/046023 A1 | 5/2006 |
| WO | 2006/071819 A1 | 7/2006 |
| WO | 2006/091450 A1 | 8/2006 |
| WO | 2006/136821 A1 | 12/2006 |
| WO | 2006/136823 A1 | 12/2006 |
| WO | 2006/136829 A2 | 12/2006 |
| WO | 2006/136830 A1 | 12/2006 |
| WO | 2006/136837 A2 | 12/2006 |
| WO | 2008/110846 A2 | 9/2008 |

OTHER PUBLICATIONS

Nagarajan, K. et al., Mechanism of Formation of p-Substituted Products in Displacement Reactions on α-Chlorodiphenylacetamides, Tetrahedron Letters, No. 22, 1968, pp. 2717-2720.

Simig, Gyula et al., Single Electron Transfer Inititated Thermal Reactions of Arylmethyl Halides, X, Acta Chimica Hungarica, 118(4), 1985, pp. 309-314.

Ajmani Subhash et al., A comprehensive structure-activity analysis of protein kinase B-alpha (Akt1) inhibitors, Journal of Molecular Graphics and Modelling, 28(7), 2010, pp. 683-694.

Murray Andrew J., Pharmacological PKA Inhibition: All May Not Be What It Seems, Science Signaling, Jun. 3, 2008, pp. 1-6.

Dorwald, Florencio Zaragoza, Side Reactions in Organic Synthesis, Wiley-VCH, 2005, p. 1 and preface.

Drewry et al. CAS 143 229871 (2005).

Schrijvers et al., Docetaxel, cisplatin and 5-fluorouracil in patients with locally advanced unresectable head and neck cancer: a phase I-II feasibility study, Annals of Oncology, vol. 15, 638-645, 2004.

Yap et al.; AT13148 Is a Novel, Oral Multi-AGC Kinase Inhibitor with Potent Pharmacodynamic and Antitumor Activity; *Clin Cancer Re;* Jul. 15, 2012; 18(14).

Marshall, Chris; Effective inhibition of actomyosin contractility by a new series of Rho-kinase inhibitors blocks multiple modes of melanoma cell migration and metastasis; PowerPoint Presentation at Antitumoral Targets Upstream and Downstream of RAS GTPases Meeting; Santander, Spain; Oct. 8-9, 2012.

* cited by examiner

COMPOSITIONS COMPRISING (S)-2-AMINO-1-(4-CHLOROPHENYL)-1-[4-(1H-PYRAZOL-4-YL)-PHENYL]-ETHANOL AS MODULATOR OF PROTEIN KINASES

CROSS REFERENCE TO RELATED APPLICATIONS

This application is a continuation application of U.S. application Ser. No. 12/531,013 (published as US 2010-0113551 A1 on May 6, 2010), which is a national phase filing under 35 U.S.C. §371 of PCT International Application No. PCT/GB2008/050180. PCT International Application No. PCT/GB2008/050180 was filed on Mar. 14, 2008, and was published under PCT Article 21(2) in English as WO 2008/110846 on Sep. 18, 2008. PCT/GB2008/050180 claimed priority from GB 0704932.3, filed on Mar. 14, 2007, and U.S. Provisional Patent Application No. 60/894,752, filed on Mar. 14, 2007. The entire contents of the prior applications are incorporated herein by reference.

This invention relates to a pyrazole-containing aryl-alkylamine compound that inhibits or modulates the activity of protein kinase B (PKB), protein kinase A (PKA), ROCK kinase or p70S6K kinase, to the use of the compound in the treatment or prophylaxis of disease states or conditions mediated by the said kinases, and to pharmaceutical compositions containing the compound. More specifically, the invention relates to a single enantiomer of 2-amino-1-(4-chloro-phenyl)-1-[4-(1H-pyrazol-4-yl)-phenyl]-ethanol, pharmaceutical compositions containing it and its therapeutic uses, as well as methods for its preparation and novel process intermediates.

BACKGROUND OF THE INVENTION

Protein kinases constitute a large family of structurally related enzymes that are responsible for the control of a wide variety of signal transduction processes within the cell (Hardie, G. and Hanks, S. (1995) *The Protein Kinase Facts Book. I and II*, Academic Press, San Diego, Calif.). The kinases may be categorized into families by the substrates they phosphorylate (e.g., protein-tyrosine, protein-serine/threonine, lipids, etc.). Sequence motifs have been identified that generally correspond to each of these kinase families (e.g., Hanks, S. K., Hunter, T., *FASEB J.*, 9:576-596 (1995); Knighton, et al., *Science*, 253:407-414 (1991); Hiles, et al., *Cell*, 70:419-429 (1992); Kunz, et al., *Cell*, 73:585-596 (1993); Garcia-Bustos, et al., *EMBO J.*, 13:2352-2361 (1994)).

Protein kinases may be characterized by their regulation mechanisms. These mechanisms include, for example, autophosphorylation, transphosphorylation by other kinases, protein-protein interactions, protein-lipid interactions, and protein-polynucleotide interactions. An individual protein kinase may be regulated by more than one mechanism.

Kinases regulate many different cell processes including, but not limited to, proliferation, differentiation, apoptosis, motility, transcription, translation and other signalling processes, by adding phosphate groups to target proteins. These phosphorylation events act as molecular on/off switches that can modulate or regulate the target protein biological function. Phosphorylation of target proteins occurs in response to a variety of extracellular signals (hormones, neurotransmitters, growth and differentiation factors, etc.), cell cycle events, environmental or nutritional stresses, etc. Appropriate protein kinases function in signalling pathways to activate or inactivate (either directly or indirectly), for example, a metabolic enzyme, regulatory protein, receptor, cytoskeletal protein, ion channel or pump, or transcription factor. Uncontrolled signalling due to defective control of protein phosphorylation has been implicated in a number of diseases, including, for example, inflammation, cancer, allergy/asthma, diseases and conditions of the immune system, diseases and conditions of the central nervous system, and angiogenesis.

Apoptosis or programmed cell death is an important physiological process which removes cells no longer required by an organism. The process is important in early embryonic growth and development allowing the non-necrotic controlled breakdown, removal and recovery of cellular components. The removal of cells by apoptosis is also important in the maintenance of chromosomal and genomic integrity of growing cell populations. There are several known checkpoints in the cell growth cycle at which DNA damage and genomic integrity are carefully monitored. The response to the detection of anomalies at such checkpoints is to arrest the growth of such cells and initiate repair processes. If the damage or anomalies cannot be repaired then apoptosis is initiated by the damaged cell in order to prevent the propagation of faults and errors. Cancerous cells consistently contain numerous mutations, errors or rearrangements in their chromosomal DNA. It is widely believed that this occurs in part because the majority of tumours have a defect in one or more of the processes responsible for initiation of the apoptotic process. Normal control mechanisms cannot kill the cancerous cells and the chromosomal or DNA coding errors continue to be propagated. As a consequence restoring these pro-apoptotic signals or suppressing unregulated survival signals is an attractive means of treating cancer.

PKB

The signal transduction pathway containing the enzymes phosphatidylinositol 3-kinase (PI3K), PDK1 and PKB amongst others, has long been known to mediate increased resistance to apoptosis or survival responses in many cells. There is a substantial amount of data to indicate that this pathway is an important survival pathway used by many growth factors to suppress apoptosis. The enzymes of the PI3K family are activated by a range of growth and survival factors e.g. EGF, PDGF and through the generation of polyphosphatidylinositols, initiates the activation of the downstream signalling events including the activity of the kinases PDK1 and protein kinase B (PKB) also known as akt. This is also true in host tissues, e.g. vascular endothelial cells as well as neoplasias. PKB is a protein ser/thr kinase consisting of a kinase domain together with an N-terminal PH domain and C-terminal regulatory domain. The enzyme $PKB_{alpha}$ (akt1) itself is phosphorylated on Thr 308 by PDK1 and on Ser 473 by 'PDK2' now believed to be constituted from the target of rapamycin (TOR) kinase and its associated protein rictor. Full activation requires phosphorylation at both sites whilst association between PIP3 and the PH domain is required for anchoring of the enzyme to the cytoplasmic face of the lipid membrane providing optimal access to substrates.

At least 10 kinases have been suggested to function as a Ser 473 kinase including mitogen-activated protein (MAP) kinase-activated protein kinase-2 (MK2), integrin-linked kinase (ILK), p38 MAP kinase, protein kinase Calpha (PKCalpha), PKCbeta, the NIMA-related kinase-6 (NEK6), the mammalian target of rapamycin (mTOR), the double-stranded DNA-dependent protein kinase (DNK-PK), and the ataxia telangiectasia mutated (ATM) gene product. Available data suggest that multiple systems may be used in cells to regulate the activation of PKB. Full activation of PKB requires phosphorylation at both sites whilst association between PIP3 and the PH domain is required for anchoring of the enzyme to the cytoplasmic face of the lipid membrane providing optimal access to substrates. PH domain mutations have recently been reported. The authors provide direct evidence for the involvement of AKT1 in human cancer by means of structural, biochemical and biological studies and demonstrate the oncogenic potential of the E17K mutation of Akt1. The mutation was identified in 5 of 61 (8%) breast, 3 of 51 (6%) colorectal and 1 of 50 (2%) ovarian cancers. (*Nature* 448, 439-444 (26 Jul. 2007)|doi:10.1038/nature05933; Received 8 Mar. 2007; Accepted 11 May 2007; Published online 4 Jul. 2007 A transforming mutation in the pleckstrin homology domain of AKT1 in cancer)

Recently, it has been reported that somatic mutations within the PI3K catalytic subunit, PIK3CA, are common (25-40%) among colorectal, gastric, breast, ovarian cancers, and high-grade brain tumors. PIK3CA mutations are a common event that can occur early in bladder carcinogenesis. In invasive breast carcinomas, PIK3CA alterations are mainly present in lobular and ductal tumours. The PI3K pathway is extensively activated in endometrial carcinomas, and that combination of PIK3CA/PTEN alterations might play an important role in development of these tumors. Tumours activated by mutations of PI3 kinase and loss of PTEN will have sustained activation of PKB and will be as a result disproportionately sensitive to inihibition by PKA/PKB inhibitors.

Activated PKB in turns phosphorylates a range of substrates contributing to the overall survival response. Whilst we cannot be certain that we understand all of the factors responsible for mediating the PKB dependent survival response, some important actions are believed to be phosphorylation and inactivation of the pro-apoptotic factor BAD and caspase 9, phosphorylation of Forkhead transcription factors e.g. FKHR leading to their exclusion from the nucleus, and activation of the NfkappaB pathway by phosphorylation of upstream kinases in the cascade.

In addition to the anti-apoptotic and pro-survival actions of the PKB pathway, the enzyme also plays an important role in promoting cell proliferation. This action is again likely to be mediated via several actions, some of which are thought to be phosphorylation and inactivation of the cyclin dependent kinase inhibitor of $p21^{Cip1/WAF1}$, and phosphorylation and activation of mTOR, a kinase controlling several aspects of cell size, growth and protein translation.

The phosphatase PTEN which dephosphorylates and inactivates polyphosphatidyl-inositols is a key tumour suppressor protein which normally acts to regulate the PI3K/PKB survival pathway. The significance of the PI3K/PKB pathway in tumourigenesis can be judged from the observation that PTEN is one of the most common targets of mutation in human tumours, with mutations in this phosphatase having been found in ~50% or more of melanomas (Guldberg et al 1997, Cancer Research 57, 3660-3663) and advanced prostate cancers (Cairns et al 1997 Cancer Research 57, 4997). These observations and others suggest that a wide range of tumour types are dependent on the enhanced PKB activity for growth and survival and would respond therapeutically to appropriate inhibitors of PKB.

There are 3 closely related isoforms of PKB called alpha, beta and gamma (AKT1, 2 and 3), which genetic studies suggest have distinct but overlapping functions. Evidence suggests that they can all independently play a role in cancer. For example PKB beta has been found to be over-expressed or activated in 10-40% of ovarian and pancreatic cancers (Bellacosa et al 1995, Int. J. Cancer 64, 280-285; Cheng et al 1996, PNAS 93, 3636-3641; Yuan et al 2000, Oncogene 19, 2324-2330), PKB alpha is amplified in human gastric, prostate and breast cancer (Staal 1987, PNAS 84, 5034-5037; Sun et al 2001, Am. J. Pathol. 159, 431-437) and increased PKB gamma activity has been observed in steroid independent breast and prostate cell lines (Nakatani et al 1999, J. Biol. Chem. 274, 21528-21532).

The PKB pathway also functions in the growth and survival of normal tissues and may be regulated during normal physiology to control cell and tissue function. Thus disorders associated with undesirable proliferation and survival of normal cells and tissues may also benefit therapeutically from treatment with a PKB inhibitor. Examples of such disorders are disorders of immune cells associated with prolonged expansion and survival of cell population leading to a prolonged or up regulated immune response. For example, T and B lymphocyte response to cognate antigens or growth factors such as interferon gamma activates the PI3K/PKB pathway and is responsible for maintaining the survival of the antigen specific lymphocyte clones during the immune response. Under conditions in which lymphocytes and other immune cells are responding to inappropriate self or foreign antigens, or in which other abnormalities lead to prolonged activation, the PKB pathway contributes an important survival signal preventing the normal mechanisms by which the immune response is terminated via apoptosis of the activated cell population. There is a considerable amount of evidence demonstrating the expansion of lymphocyte populations responding to self antigens in autoimmune conditions such as multiple sclerosis and arthritis. Expansion of lymphocyte populations responding inappropriately to foreign antigens is a feature of another set of conditions such as allergic responses and asthma. In summary inhibition of PKB could provide a beneficial treatment for immune disorders.

Other examples of inappropriate expansion, growth, proliferation, hyperplasia and survival of normal cells in which PKB may play a role include but are not limited to atherosclerosis, cardiac myopathy and glomerulonephritis.

In addition to the role in cell growth and survival, the PKB pathway functions in the control of glucose metabolism by insulin. Available evidence from mice deficient in the alpha and beta isoforms of PKB suggests that this action is mediated by the beta isoform primarily. As a consequence, modulators of PKB activity may also find utility in diseases in which there is a dysfunction of glucose metabolism and energy storage such as diabetes, metabolic disease and obesity.

PKA

Cyclic AMP-dependent protein kinase (PKA) is a serine/threonine protein kinase that phosphorylates a wide range of substrates and is involved in the regulation of many cellular processes including cell growth, cell differentiation, ion-channel conductivity, gene transcription and synaptic release of neurotransmitters. In its inactive form, the PKA holoenzyme is a tetramer comprising two regulatory subunits and two catalytic subunits.

PKA acts as a link between G-protein mediated signal transduction events and the cellular processes that they regulate. Binding of a hormone ligand such as glucagon to a transmembrane receptor activates a receptor-coupled G-protein (GTP-binding and hydrolyzing protein). Upon activation, the alpha subunit of the G protein dissociates and binds to and activates adenylate cyclase, which in turn converts ATP to cyclic-AMP (cAMP). The cAMP thus produced then binds to the regulatory subunits of PKA leading to dissociation of the associated catalytic subunits. The catalytic subunits of PKA, which are inactive when associated with the regulatory sub-units, become active upon dissociation and take part in the phosphorylation of other regulatory proteins.

For example, the catalytic sub-unit of PKA phosphorylates the kinase Phosphorylase Kinase which is involved in the phosphorylation of Phosphorylase, the enzyme responsible for breaking down glycogen to release glucose. PKA is also involved in the regulation of glucose levels by phosphorylating and deactivating glycogen synthase. Thus, modulators of PKA activity (which modulators may increase or decrease PKA activity) may be useful in the treatment or management of diseases in which there is a dysfunction of glucose metabolism and energy storage such as diabetes, metabolic disease and obesity.

PKA has also been established as an acute inhibitor of T cell activation Anndahl et al, have investigated the possible role of PKA type I in HIV-induced T cell dysfunction on the basis that T cells from HIV-infected patients have increased levels of cAMP and are more sensitive to inhibition by cAMP analogues than are normal T cells. From their studies, they concluded that increased activation of PKA type I may contribute to progressive T cell dysfunction in HIV infection and that PKA type I may therefore be a potential target for immunomodulating therapy.—Aandahl, E. M., Aukrust, P., Skålhegg, B. S., Müller, F., Frøland, S. S., Hansson, V., Taskén, K. *Protein kinase A type I antagonist restores immune responses of T cells from HIV-infected patients. FASEB J.* 12, 855-862 (1998).

It has also been recognised that mutations in the regulatory sub-unit of PKA can lead to hyperactivation in endocrine tissue.

Because of the diversity and importance of PKA as a messenger in cell regulation, abnormal responses of cAMP can lead to a variety of human diseases derived from this, such as irregular cell growth and proliferation (Stratakis, C. A.; Cho-Chung, Y. S.; Protein Kinase A and human diseases. *Trends Endrocri. Metab.* 2002, 13, 50-52). Over-expression of PKA has been observed in a variety of human cancer cells including those from ovarian, breast and colon patients. Inhibition of PKA would therefore be an approach to treatment of cancer (Li, Q.; Zhu, G-D.; *Current Topics in Medicinal Chemistry,* 2002, 2, 939-971).

For a review of the role of PKA in human disease, see for example, *Protein Kinase A and Human Disease*, Edited by Constantine A. Stratakis, Annals of the New York Academy of Sciences, Volume 968, 2002, ISBN 1-57331-412-9.

ROCK Kinases

The ROCK kinase family comprises two known members: ROCK1 and ROCK2:
ROCK1. Synonyms: Rho-associated protein kinase 1; p160 ROCK; P160 ROK; p160 ROCK-1, Rho-associated, coiled-coil containing protein kinase 1; Rho kinase 1; ROK beta.
ROCK2. Synonyms: Rho-associated protein kinase 2; p164 ROCK; p164 ROK; p164 ROCK-2; Rho-associated, coiled-coil containing protein kinase 2, Rho kinase 2; ROK alpha.

The process of metastasis involves a restructuring of the cytoskeleton as well as cell-cell and cell-matrix adhesions allowing cells to break away from the tumor mass, invade local tissue, and ultimately spread throughout the body. These effects on cell morphology and adhesion are regulated by members of the Rho GTPase family.

Activated RhoA is capable of interacting with several effecter proteins including the ROCK kinases ROCK1 and ROCK2. ROCK1 and ROCK2 can be activated by the RhoA-GTP complex via physical association. Activated ROCKs phosphorylate a number of substrates and play important roles in pivotal cellular functions. The substrates for ROCKs include myosin binding subunit of myosin light chain phosphatase (MBS, also named MYPT1), adducin, moesin, myosin light chain (MLC), LIM kinase, and the transcription factor FHL. The phosphorylation of theses substrates modulate the biological activity of the proteins and provide a means to alter a cell's response to external stimuli.

Elevated expression of RhoA and RhoC, as well as the Rho effector proteins ROCK1 and ROCK2, are commonly observed in human cancers, including in the progression of testicular germ cell tumours, small breast carcinomas with metastatic ability, invasion and metastasis of bladder cancer, tumor progression in ovarian carcinoma.

Progression of tumors to invasive and metastatic forms requires that tumor cells undergo dramatic morphologic changes, a process regulated by Rho GTPases. Actomyosin contractility is a mechanism by which cells exert locomotory force against their environment. Signalling downstream of the small GTPase Rho increases contractility through ROCK-mediated regulation of myosin-II light chain (MLC2) phosphorylation.

The ROCK kinases are thought to participate in the induction of focal adhesions and stress fibers and to mediate calcium sensitization of smooth muscle contraction by enhancing phosphorylation of the regulatory light chain of myosin.

In vivo studies have also shown that ROCK inhibition reduced the invasiveness of several tumor cell lines. ROCK inhibitors, such as Y-27632 or WF-536, have been used in some studies to demonstrate these properties.

Inhibitors of ROCKs have been suggested for use in the treatments of a variety of diseases. These include cardiovascular diseases such as hypertension, chronic and congestive heart failure, cardiac hypertrophy, restenosis, chronic renal failure and atherosclerosis. Also, because of its muscle relaxing properties, inhibitors may also be suitable for asthma, male erectile dysfunction, female sexual dysfunction and over-active bladder I syndrome.

ROCK inhibitors have been shown to possess anti-inflammatory properties. Thus they can be used as treatment for neuroinflammatory diseases such as stroke, multiple sclerosis, Alzheimer's disease, Parkinson's disease, amyotrophic lateral sclerosis and inflammatory pain, as well as other inflammatory diseases such as rheumatoid arthritis, irritable bowel syndrome, and inflammatory bowel disease. Based on their neurite outgrowth inducing effects, ROCK inhibitors could be useful drugs for neuronal regeneration, inducing new axonal growth and axonal rewiring across lesions within the CNS. ROCK inhibitors are therefore likely to be useful for regenerative treatment of CNS disorders such as spinal cord injury, acute neuronal injury (stroke, traumatic brain injury), Parkinson's disease, Alzheimers disease and other neurodegenerative disorders. Since ROCK inhibitors reduce cell proliferation and cell migration, they could be useful in treating cancer and tumor metastasis. Finally, there is evidence to suggest that ROCK inhibitors suppress cytoskeletal rearrangement upon virus invasion, thus they also have potential therapeutic value in anti-viral and anti-bacterial applications. ROCK inhibitors are also useful for the treatment of insulin resistance and diabetes.

ROCK Inhibitor Y-27632

Adhesion of tumour cells to host cell layers and subsequent transcellular migration are pivotal steps in cancer invasion and metastasis. The small GTPase Rho controls cell adhesion and motility through reorganization of the actin cytoskeleton and regulation of actomyosin contractility. Cultured rat MM1 hepatoma cells migrate in a serum-dependent, Rho-mediated manner, through a mesothelial cell monolayer in vitro. Among several proteins isolated as putative target molecules of Rho, the ROCK kinases are thought to participate in the induction of focal adhesions and stress fibres in cultured cells, and to mediate calcium sensitization of smooth muscle contraction by enhancing phosphorylation of the regulatory light chain of myosin. Transfection of MM1 cells with cDNA encoding a dominant active mutant of ROCK conferred invasive activity independently of serum and Rho. In contrast, expression of a dominant negative, kinase-defective ROCK mutant substantially attenuated the invasive phenotype.

A specific ROCK inhibitor (Y-27632) blocked both Rho-mediated activation of actomyosin and invasive activity of these cells. Furthermore, continuous delivery of this inhibitor using osmotic pumps considerably reduced the dissemination of MM1 cells implanted into the peritoneal cavity of syngeneic rats. These results indicate that ROCK plays an essential part in tumor cell invasion, and demonstrate its potential as a therapeutic target for the prevention of cancer invasion and metastasis.

VEGF induced the activation of RhoA and recruited RhoA to the cell membrane of human ECs. This increase in RhoA activity is necessary for the VEGF-induced reorganization of the F-actin cytoskeleton, as demonstrated by adenoviral transfection of dominant-negative RhoA. Rho kinase mediated this effect of RhoA, as was demonstrated by the use of Y-27632, a specific inhibitor of Rho kinase. Inhibition of Rho kinase prevented the VEGF-enhanced EC migration in response to mechanical wounding but had no effect on basal EC migration. Furthermore, in an in vitro model for angiogenesis, inhibition of either RhoA or Rho kinase attenuated the VEGF-mediated ingrowth of ECs in a 3-dimensional fibrin matrix.

CONCLUSIONS: VEGF-induced cytoskeletal changes in ECs require RhoA and Rho kinase, and activation of RhoA/Rho kinase signalling is involved in the VEGF-induced in vitro EC migration and angiogenesis.

Y-27632 can relax smooth muscle and increase vascular blood flow. Y-27632 is a small molecule that can enter cells and is not toxic in rats after oral administration of 30 mg/kg for 10 days. Effective doses for the use of this compound are approximately 30 uM. It reduces blood pressure in hypertensive rats, but does not affect blood pressure in normal rats. This has led to the identification of Rho signalling antagonists in treatment of hypertension (Somlyo, 1997 Nature 389:908; Uehata et al., 1997 Nature 389:990).

The use of a specific inhibitor of ROCK, Y-27632 (Uehata, et al., Nature, 389, 990 994, 1997, Davies, et al., Biochemical Journal., 351, 95-105, 2000, and Ishizaki, et al., Molecular Pharmacology., 57, 976-983, 2000), has demonstrated a role for this enzyme in $Ca^{2+}$ independent regulation of contraction in a number of tissues, including vascular (Uehata, et al., Nature., 389, 990-994, 1997), airway (Ilikuka et al., European Journal of 30 Pharmacology., 406, 273-279, 2000) and genital (Chitaley et al., Nature Medicine., 7(1), 119-122, 2001) smooth muscles. In addition, Jezior et al. British Journal of Pharmacology., 134, 78-87, 2001 have shown that Y-27632 attenuates bethanechol-evoked contractions in isolated rabbit urinary 35 bladder smooth muscle.

The Rho kinase inhibitor Y-27632 has been tested for the following disease applications:
- Hypertension (Uehata et al., 1997 IBID; Chitaley et al., 2001a IBID; Chrissobolis and 15 Sobey, 2001 C. Circ. Res 88:774)
- Asthma (Iizuka et al., 2000 Eur. J. Pharmacol 406:273; Nakahara et al. Eur. J. Pharmacol 389:103, 2000)
- Pulmonary vasoconstriction (Takamura et al., 2001 Hepatology 33:577)
- Vascular disease (Miyata et al., 2000 Thromb Vasc Biol 20:2351; Robertson et al., 2000 Br. J. Pharmacol 131:5)
- Penile erectile dysfunction (Chitaley et al., 2001b Nature Medicine 7:119; Mills et al., 2001 J. Appl. Physiol. 91: 1269; Rees et al., Br. J. Pharmacol 133:455 2001)
- Glaucoma (Honjo et al., 2001 Methods Enzymol 42:137; Rao et al., 2001 Invest. Opthalmol. Urs. Sci. 42:1029)
- Cell transformation (Sahai et al., 1999 Curr. Biol. 9:136-5)
- Prostate cancer metastasis (Somlyo et al., 2000 BBRC 269:652)
- Hepatocellular carcinoma and metastasis (Imamura et al., 2000; Takamura et al., 2001)
- Liver fibrosis (Tada et al., 2001 J. Hepatol 34:529; Wang et al., 2001 Am. J. Respir. Cell Mol. Biol. 25:628)
- Kidney fbrosis (Ohlci et al., J. Heart Lung Transplant 20:956 2001)
- Cardioprotection and allograft survival (Ohlci et al., 2001 IBID)
- Cerebral vasospasm (Sato et al., 2000 Circ. Res 87: 195).

ROCK Kinase and Cardiovascular Disease

There is growing evidence that ROCKs, the immediate downstream targets of the small guanosine triphosphate-binding protein Rho, may contribute to cardiovascular disease. ROCKs play a central role in diverse cellular functions such as smooth muscle contraction, stress fiber formation and cell migration and proliferation. Overactivity of ROCKs is observed in cerebral ischemia, coronary vasospasm, hypertension, vascular inflammation, arteriosclerosis and atherosclerosis. ROCKs, therefore, may be an important and still relatively unexplored therapeutic target in cardiovascular disease. Recent experimental and clinical studies using ROCK inhibitors such as Y-27632 and fasudil have revealed a critical role of ROCKs in embryonic development, inflammation and oncogenesis. This review will focus on the potential role of ROCKs in cellular functions and discuss the prospects of ROCK inhibitors as emerging therapy for cardiovascular diseases.

Abnormal smooth-muscle contractility may be a major cause of disease states such as hypertension, and a smooth-muscle relaxant that modulates this process would be useful therapeutically. Smooth-muscle contraction is regulated by the cytosolic $Ca^{2+}$ concentration and by the $Ca^{2+}$ sensitivity of myofilaments: the former activates myosin light-chain kinase and the latter is achieved partly by inhibition of myosin phosphatase.

Rho signaling pathways in vascular smooth muscle cells are highly activated in hypertension, a condition associated with a variety of vascular diseases, including restenosis injury and atherosclerosis.

Hypertension is a cardiovascular disorder characterized by increased peripheral vascular resistance and/or vascular structural remodeling. Recently, rapidly growing evidence from hypertensive animal models suggests that small GTPase Rho and its downstream effector, Rho-kinase, play an important role in the pathogenesis of hypertension. Activation of the Rho/Rho-kinase pathway is essential for smooth muscle contractility in hypertension. A greater RhoA expression and an enhanced RhoA activity have been observed in aortas of hypertensive rats, such as genetic spontaneously hypertensive rats and N(omega)-nitro-L-arginine methyl ester-induced hypertension.

ROCK Kinase and Neurological Diseases

Abnormal activation of the Rho/ROCK pathway has been observed in various disorders of the central nervous system. Injury to the adult vertebrate brain and spinal cord activates ROCKs, thereby inhibiting neurite growth and sprouting. Inhibition of ROCKs results in accelerated regeneration and enhanced functional recovery after spinal-cord injury in mammals, and inhibition of the Rho/ROCK pathway has also proved to be efficacious in animal models of stroke, inflammatory and demyelinating diseases, Alzheimer's disease and neuropathic pain. ROCK inhibitors therefore have potential for preventing neurodegeneration and stimulating neuroregeneration in various neurological disorders.

The development of a neuron requires a series of steps that begins with migration from its birth place and initiation of process outgrowth, and ultimately leads to differentiation and the formation of connections that allow it to communicate with appropriate targets. Over the past several years, it has become clear that the Rho family of GTPases and related molecules play an important role in various aspects of neuronal development, including neurite outgrowth and differentiation, axon pathfinding, and dendritic spine formation and maintenance.

One common denominator for both neurite outgrowth inhibition and neurite repulsion is actin rearrangements within the growth cone. Central to the regulation of the actin cytoskeleton in both neuronal and non-neuronal cells is the Rho family of small GTPases. Rho family members cycle between an inactive GDP-bound form and an active GTP-bound form. Several lines of evidence suggest that manipulating the activity state of Rho GTPases may modulate growth cone collapse and neurite outgrowth inhibition.

More recently, behaviorally, inactivation of Rho pathway can induce rapid recovery of locomotion and progressive recuperation of forelimb-hindlimb coordination. These findings provide evidence that the Rho signaling pathway is a potential target for therapeutic interventions after spinal cord injury.

p70S6K Kinase

The 70 kDa ribosomal protein kinase p70S6K (also known as SK6, p70/p85 S6 kinase, p70/p85 ribosomal S6 kinase and pp 70s6k) is a member of the AGC subfamily of protein kinases. p70S6K is a serine-threonine kinase that is a component of the phosphatidylinositol 3 kinase (PI3K)/AKT pathway. p70S6K is downstream of PI3K, and activation occurs through phosphorylation at a number of sites in response to numerous mitogens, hormones and growth factors. This response may be under the control of mTOR since rapamycin acts to inhibit p70S6K activity and blocks protein synthesis, specifically as a result of a down-regulation of translation of these mRNA's encoding ribosomal proteins. p70S6K is also regulated by PI3K and its downstream target AKT. Wortmannin and rapamycin cause a decrease in p70S6K phosphorylation at sites dependent of the PI3K pathway. Mutant p70S6K is inhibited by wortmannin but not by rapamycin suggesting that the PI3K pathway can exhibit effects on p70S6K independent of the regulation of mTOR activity.

The enzyme p70S6K modulates protein synthesis by phosphorylation of the S6 ribosomal protein. S6 phosphorylation correlates with increased translation of mRNAs encoding components of the translational apparatus, including ribosomal proteins and translational elongation factors whose increased expression is essential for cell growth and proliferation. These mRNAs contain an oligopyrimidine tract at their 5' transcriptional start (termed 5'TOP), which has been shown to be essential for their regulation at the translational level.

In addition to its involvement in translation, p70S6K activation has also been implicated in cell cycle control, neuronal cell differentiation, regulation of cell motility and a cellular response that is important in tumor metastases, the immune response and tissue repair. Antibodies to p70S6K abolish the mitogenic response driven entry of rat fibroblasts into S phase, indication that p70S6K function is essential for the progression from G1 to S phase in the cell cycle. Furthermore inhibition of cell cycle proliferation at the G1 to S phase of the cell cycle by rapamycin has been identified as a consequence of inhibition of the production of the hyperphosphorylated, activated form of p70S6K.

The tumor suppressor LKB1 activates AMPK which phosphorylates the TSC1/2 complex in the mTOR/p70S6K pathway, therefore feeds into p70S6K through a PKB independent pathway. Mutations in LKB1 cause Peutz-Jeghers syndrome (PJS), where patients with PJS are 15 times more likely to develop cancer than the general population. In addition, ⅓ of lung adenocarcinomas harbor inactivating LKB1 mutations.

A role for p70S6K in tumor cell proliferation and protection of cells from apoptosis is supported based on its participation in growth factor receptor signal transduction, overexpression and activation in tumor tissues. For example, Northern and Western analyses revealed that amplification of the PS6K gene was accompanied by corresponding increases in mRNA and protein expression, respectively (Cancer Res. (1999) 59: 1408-11—Localization of PS6K to Chromosomal Region 17q23 and Determination of Its Amplification in Breast Cancer).

Chromosome 17q23 is amplified in up to 20% of primary breast tumors, in 87% of breast tumors containing BRCA2 mutations and in 50% of tumors containing BRCA1 mutations, as well as other cancer types such as pancreatic, bladder and neuroblastoma (see M Barlund, 0 Monni, J Kononen, R Cornelison, J Torhorst, G Sauter, O-P Kallioniemi and Kallioniemi A, Cancer Res., 2000, 60:5340-5346). It has been shown that 17q23 amplifications in breast cancer involve the PAT1, RAD51C, PS6K, and SIGMA1B genes (Cancer Res. (2000): 60, pp. 5371-5375).

The p70S6K gene has been identified as a target of amplification and overexpression in this region, and statistically significant association between amplification and poor prognosis has been observed.

Clinical inhibition of p70S6K activation was observed in renal carcinoma patients treated with CCI-779 (rapamycin ester), an inhibitor of the upstream kinase mTOR. A significant linear association between disease progression and inhibition of p70S6K activity was reported.

p70S6K has been implicated in metabolic diseases and disorders. It was reported that the absence of p70S6 protects against age- and diet-induced obesity while enhancing insulin sensitivity. A role for p70S6K in metabolic diseases and disorders such as obesity, diabetes, metabolic syndrome, insulin resistance, hyperglycemia, hyperaminoacidemia, and hyperlipidmia is supported based upon the findings.

Pyrazole Compounds Having PKB and PKA Inhibiting Activity

Several classes of compounds have been disclosed as having PKA and PKB inhibitory activity. For example, WO 2005/061463 (Astex) discloses pyrazole compounds having PKB and PKA inhibiting activity and one particular compound exemplified is 2-amino-1-(4-chloro-phenyl)-1-[4-(1H-pyrazol-4-yl)-phenyl]-ethanol. This compound, the structure of which is shown below, has a chiral centre at the carbon atom marked with an asterisk.

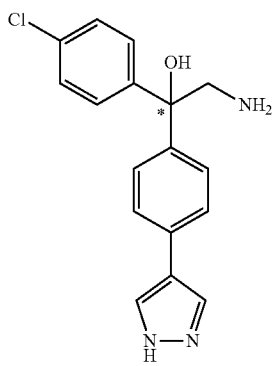 [SMILES: NCC(O)(c1ccc(Cl)cc1)c1ccc(-c2cn[nH]c2)cc1]

The compound described in Example 84 of WO 2005/061463 is a racemic mixture of the two possible enantiomers. According to Examples 106 and 107, the compound of Example 84 has $IC_{50}$ values in the in vitro PKA and PKB assays respectively of less than 1 micromolar in each case.

WO 2005/061463 also discloses and exemplifies a number of individual enantiomers, as follows:

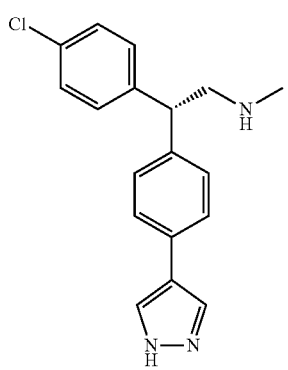

WO 2005/061463 - Example 22

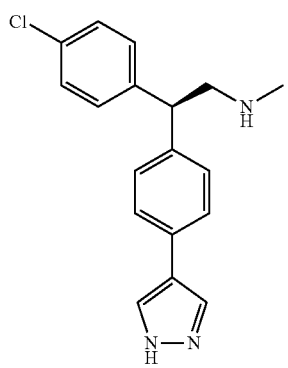

WO 2005/061463 - Example 23

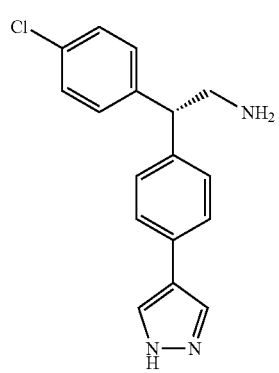

WO 2005/061463 - Example 30

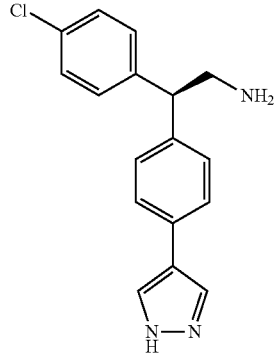

WO 2005/061463 - Example 31

Isomers A and B constitute one pair of enantiomers and Isomers C and D constitute another pair of enantiomers.

Tests carried out by the present applicants have established that Isomer A is 10 fold more active against PKB than its antipode Isomer B in a binding assay. Similarly, Isomer C is about 10 fold more active than its antipode Isomer D in a binding assay. However, in a mechanistic cellular ELISA assay, isomers C and D are essentially equipotent.

SUMMARY OF THE INVENTION

Based on the activities of isomers A, B, C and D described above, it might be anticipated that the individual enantiomers of the Compound of Example 84 in WO 2005/061463 would also show a relatively small difference in activity.

However, it has now been found most unexpectedly that the S-enantiomer of 2-amino-1-(4-chloro-phenyl)-1-[4-(1H-pyrazol-4-yl)-phenyl]-ethanol is 100 fold more active (as determined by a radiometric binding assay) against PKB than the corresponding R-enantiomer. Moreover, whereas the isomers C and D above are essentially equipotent in the mechanistic cellular assay, and the S-enantiomer of 2-amino-1-(4-chloro-phenyl)-1-[4-(1H-pyrazol-4-yl)-phenyl]-ethanol has good activity in this assay, the R-enantiomer has no measurable activity. When compared to the properties of the known individual enantiomers A, B, C and D above, the differences in activity between the S- and R-enantiomers of 2-amino-1-(4-chloro-phenyl)-1-[4-(1H-pyrazol-4-yl)-phenyl]-ethanol are very surprising and could not have been predicted.

It follows from the above that the S-enantiomer of 2-amino-1-(4-chloro-phenyl)-1-[4-(1H-pyrazol-4-yl)-phenyl]-ethanol has substantial advantages over its antipode, the R-isomer.

Accordingly, in a first aspect, the invention provides a composition comprising (S)2-amino-1-(4-chloro-phenyl)-1-[4-(1H-pyrazol-4-yl)-phenyl]-ethanol, wherein the composition is either substantially free of (R)2-amino-1-(4-chloro-phenyl)-1-[4-(1H-pyrazol-4-yl)-phenyl]-ethanol or the composition contains a mixture of the (S) and (R) enantiomers in which the (S) enantiomer predominates.

The invention also provides a composition comprising 2-amino-1-(4-chloro-phenyl)-1-[4-(1H-pyrazol-4-yl)-phenyl]-ethanol or a salt, solvate, tautomer or N-oxide thereof, at least 75% of which is in the S-enantiomeric form.

The term "composition" as used herein refers to a composition of matter and includes compositions which consist solely of 2-amino-1-(4-chloro-phenyl)-1-[4-(1H-pyrazol-4-yl)-phenyl]-ethanol as well as compositions which contain additional components. According to the invention, at least 75% of all of the 2-amino-1-(4-chloro-phenyl)-1-[4-(1H-pyrazol-4-yl)-phenyl]-ethanol present in the composition must be in the S-enantiomeric form. The compositions may be referred to herein for convenience as "the compositions of the invention" or "the compositions as defined herein" or "the compositions".

The amount of (S)-2-amino-1-(4-chloro-phenyl)-1-[4-(1H-pyrazol-4-yl)-phenyl]-ethanol present in a given composition relative to the total amount of 2-amino-1-(4-chloro-phenyl)-1-[4-(1H-pyrazol-4-yl)-phenyl]-ethanol of both enantiomeric forms present in the composition may be expressed as the "enantiomeric purity". For example, if 75% of the total 2-amino-1-(4-chloro-phenyl)-1-[4-(1H-pyrazol-4-yl)-phenyl]-ethanol present in the composition present in the form of the S-enantiomer, then the enantiomeric purity is 75%.

Preferably, the (S)-2-amino-1-(4-chloro-phenyl)-1-[4-(1H-pyrazol-4-yl)-phenyl]-ethanol has an enantiomeric purity of at least 80%, more preferably at least 85%, or at least 90%, or at least 91%, 92%, 93%, 94%, 95%, 96%, 97%, 98%, 99% or 99.5%.

In a preferred embodiment, greater than 98% of the 2-amino-1-(4-chloro-phenyl)-1-[4-(1H-pyrazol-4-yl)-phenyl]-ethanol is in the S-enantiomeric form.

In another embodiment, at least 99.9% of the 2-amino-1-(4-chloro-phenyl)-1-[4-(1H-pyrazol-4-yl)-phenyl]-ethanol is in the S-enantiomeric form.

Preferably, substantially no (R)-2-amino-1-(4-chloro-phenyl)-1-[4-(1H-pyrazol-4-yl)-phenyl]-ethanol is present in the composition. The term "substantially no (R)-2-amino-1-(4-chloro-phenyl)-1-[4-(1H-pyrazol-4-yl)-phenyl]-ethanol is present in the composition" as used in this application means that no R-enantiomer can be detected using the analytical methods described herein In one embodiment, the composition is a pharmaceutical composition containing the (S)-2-amino-1-(4-chloro-phenyl)-1-[4-(1H-pyrazol-4-yl)-phenyl]-ethanol or a salt, solvate, tautomer or N-oxide thereof, and a pharmaceutically acceptable carrier.

In another embodiment, the composition consists of (S)-2-amino-1-(4-chloro-phenyl)-1-[4-(1H-pyrazol-4-yl)-phenyl]-ethanol or a salt, solvate, tautomer or N-oxide thereof, in substantially pure form, i.e. containing less than 0.5%, more preferably less than 0.1% and most preferably less than 0.01% impurities.

In a preferred embodiment, no single impurity is present in the composition in an amount corresponding to more than 0.2% by weight, and preferably no more than 0.1% by weight.

In another embodiment, where the identity of the impurity is known, it is preferred that the impurity is not present in the composition in an amount greater than 0.5%, or greater than 0.4%, or greater than 0.3%, or greater than 0.2%, or greater than 0.1%, or greater than 0.05%, or greater than 0.01%.

The (S)-2-amino-1-(4-chloro-phenyl)-1-[4-(1H-pyrazol-4-yl)-phenyl]-ethanol is represented by formula (I) below, and may be referred to herein as the "compound of formula (I)" or "the S-enantiomer".

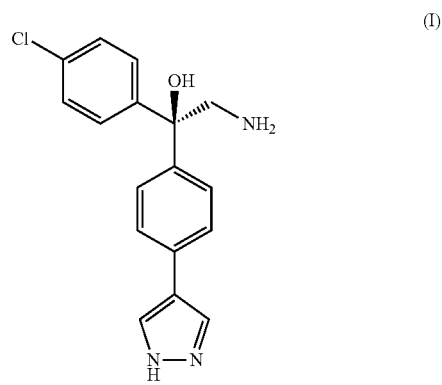 [SMILES: NC[C@@](O)(c1ccc(Cl)cc1)c1ccc(-c2cn[nH]c2)cc1]

(I)

The (R)-2-amino-1-(4-chloro-phenyl)-1-[4-(1H-pyrazol-4-yl)-phenyl]-ethanol may be referred to for convenience herein as "the R-enantiomer".

The terms "R" and "S" as used herein refer to the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.*, 1966, 5, 385-415.

The compositions of the invention can be prepared by partially or fully resolving a mixture of (S) and (R) enantiomers of 2-amino-1-(4-chloro-phenyl)-1-[4-(1H-pyrazol-4-yl)-phenyl]-ethanol, for example using chiral chromatography, as described below.

The (S)-2-amino-1-(4-chloro-phenyl)-1-[4-(1H-pyrazol-4-yl)-phenyl]-ethanol (i.e. the compound of formula (I)) has protein kinase B (PKB) and/or protein kinase A (PKA) inhibiting or modulating activity, and is therefore useful in preventing or treating disease states or conditions mediated by PKB and/or PKA.

In another aspect, the invention provides a compound of the formula (I), i.e. (S)-2-amino-1-(4-chloro-phenyl)-1-[4-(1H-pyrazol-4-yl)-phenyl]-ethanol, or a salt, solvate, tautomer or N-oxide thereof, in substantially pure form, i.e. containing less than 0.5%, more preferably less than 0.1% and most preferably less than 0.01% impurities.

In one embodiment, the compound is other than an N-oxide and is selected from the free base or a salt, solvate or tautomer thereof.

In another embodiment, the compound of formula (I) or a tautomer thereof is in the form of the free base.

In a further embodiment, the compound of formula (I) or a tautomer thereof is in the form of a salt. One particular salt prepared in accordance with the invention is the salt formed with hydrochloric acid.

In further aspects, the invention provides:
A composition or compound of formula (I), or a salt, solvate, tautomer or N-oxide thereof as defined herein for use in the prophylaxis or treatment of a disease state or condition mediated by protein kinase B.
The use of a composition or compound of formula (I), or a salt, solvate, tautomer or N-oxide thereof as defined herein for the manufacture of a medicament for the prophylaxis or treatment of a disease state or condition mediated by protein kinase B.

A method for the prophylaxis or treatment of a disease state or condition mediated by protein kinase B, which method comprises administering to a subject in need thereof a composition or compound of formula (I), or a salt, solvate, tautomer or N-oxide thereof as defined herein.

A composition or compound of formula (I), or a salt, solvate, tautomer or N-oxide thereof as defined herein for use in treating a disease or condition comprising or arising from abnormal cell growth or abnormally arrested cell death in a mammal.

The use of a composition or compound of formula (I), or a salt, solvate, tautomer or N-oxide thereof as defined herein for the manufacture of a medicament for treating a disease or condition comprising or arising from abnormal cell growth or abnormally arrested cell death in a mammal.

A method for treating a disease or condition comprising or arising from abnormal cell growth in a mammal, which method comprises administering to the mammal a composition or compound of formula (I), or a salt, solvate, tautomer or N-oxide thereof as defined herein in an amount effective in inhibiting abnormal cell growth or abnormally arrested cell death.

A method for alleviating or reducing the incidence of a disease or condition comprising or arising from abnormal cell growth or abnormally arrested cell death in a mammal, which method comprises administering to the mammal a composition or compound of formula (I), or a salt, solvate, tautomer or N-oxide thereof as defined herein in an amount effective in inhibiting abnormal cell growth.

A method for treating a disease or condition comprising or arising from abnormal cell growth or abnormally arrested cell death in a mammal, the method comprising administering to the mammal a composition or compound of formula (I), or a salt, solvate, tautomer or N-oxide thereof as defined herein in an amount effective to inhibit protein kinase B activity.

A composition or compound of formula (I), or a salt, solvate, tautomer or N-oxide thereof as defined herein for use in inhibiting protein kinase B.

A method of inhibiting protein kinase B, which method comprises contacting the kinase with a kinase-inhibiting composition or compound of formula (I), or a salt, solvate, tautomer or N-oxide thereof as defined herein A composition or compound of formula (I), or a salt, solvate, tautomer or N-oxide thereof as defined herein for use in modulating a cellular process (for example cell division) by inhibiting the activity of a protein kinase B and/or protein kinase A.

The use of a composition or compound of formula (I), or a salt, solvate, tautomer or N-oxide thereof as defined herein for the manufacture of a medicament for modulating a cellular process (for example cell division) by inhibiting the activity of a protein kinase B and/or protein kinase A.

A method of modulating a cellular process (for example cell division) by inhibiting the activity of a protein kinase B and/or protein kinase A using a composition or compound of formula (I), or a salt, solvate, tautomer or N-oxide thereof as defined herein.

A composition or compound of formula (I), or a salt, solvate, tautomer or N-oxide thereof as defined herein for use in the prophylaxis or treatment of a disease state or condition mediated by protein kinase A.

The use of a composition or compound of formula (I), or a salt, solvate, tautomer or N-oxide thereof as defined herein for the manufacture of a medicament for the prophylaxis or treatment of a disease state or condition mediated by protein kinase A.

A method for the prophylaxis or treatment of a disease state or condition mediated by protein kinase A, which method comprises administering to a subject in need thereof a composition or compound of formula (I), or a salt, solvate, tautomer or N-oxide thereof as defined herein.

A method for treating a disease or condition comprising or arising from abnormal cell growth or abnormally arrested cell death in a mammal, the method comprising administering to the mammal a composition or compound of formula (I), or a salt, solvate, tautomer or N-oxide thereof as defined herein in an amount effective to inhibit protein kinase A activity.

A composition or compound of formula (I), or a salt, solvate, tautomer or N-oxide thereof as defined herein for inhibiting protein kinase A.

A method of inhibiting protein kinase A, which method comprises contacting the kinase with a kinase-inhibiting composition or compound of formula (I), or a salt, solvate, tautomer or N-oxide thereof as defined herein A method of modulating a cellular process (for example cell division) by inhibiting the activity of a protein kinase A using a composition or compound of formula (I), or a salt, solvate, tautomer or N-oxide thereof as defined herein.

The use of a composition or compound of formula (I), or a salt, solvate, tautomer or N-oxide thereof as defined herein for the manufacture of a medicament for the prophylaxis or treatment of a disease state or condition arising from abnormal cell growth or abnormally arrested cell death.

A pharmaceutical composition comprising a composition or compound of formula (I), or a salt, solvate, tautomer or N-oxide thereof as defined herein and a pharmaceutically acceptable carrier.

A composition or compound of formula (I), or a salt, solvate, tautomer or N-oxide thereof as defined herein for use in medicine.

The use of a composition or compound of formula (I), or a salt, solvate, tautomer or N-oxide thereof as defined herein for the manufacture of a medicament for the prophylaxis or treatment of any one of the disease states or conditions disclosed herein.

A method for the treatment or prophylaxis of any one of the disease states or conditions disclosed herein, which method comprises administering to a patient (e.g. a patient in need thereof) a compound (e.g. a therapeutically effective amount) of composition or compound of formula (I), or a salt, solvate, tautomer or N-oxide thereof as defined herein.

A method for alleviating or reducing the incidence of a disease state or condition disclosed herein, which method comprises administering to a patient (e.g. a patient in need thereof) a compound (e.g. a therapeutically effective amount) of a composition or compound of formula (I), or a salt, solvate, tautomer or N-oxide thereof as defined herein.

A method for the diagnosis and treatment of a disease state or condition mediated by protein kinase B, which method comprises (i) screening a patient to determine whether a disease or condition from which the patient is or may be suffering is one which would be susceptible to treatment with a compound having activity against protein kinase B; and (ii) where it is indicated that the disease or condition from which the patient is thus susceptible, thereafter administering to the patient a composition or compound of formula (I), or a salt, solvate, tautomer or N-oxide thereof as defined herein.

The use of a composition or compound of formula (I), or a salt, solvate, tautomer or N-oxide thereof as defined herein for the manufacture of a medicament for the treatment or prophylaxis of a disease state or condition in a patient who has been screened and has been determined as suffering from, or being at risk of suffering from, a disease or condition which would be susceptible to treatment with a compound having activity against protein kinase B.

A composition or compound of formula (I), or a salt, solvate, tautomer or N-oxide thereof as defined herein for use in the treatment or prophylaxis of a disease state or condition in a patient who has been screened and has been determined as suffering from, or being at risk of suffering from, a disease or condition which would be susceptible to treatment with a compound having activity against protein kinase B.

A method for the diagnosis and treatment of a disease state or condition mediated by protein kinase A, which method comprises (i) screening a patient to determine whether a disease or condition from which the patient is or may be suffering is one which would be susceptible to treatment with a compound having activity against protein kinase A; and (ii) where it is indicated that the disease or condition from which the patient is thus susceptible, thereafter administering to the patient a composition or compound of formula (I), or a salt, solvate, tautomer or N-oxide thereof as defined herein.

A composition or compound of formula (I), or a salt, solvate, tautomer or N-oxide thereof as defined herein for use in the treatment or prophylaxis of a disease state or condition in a patient who has been screened and has been determined as suffering from, or being at risk of suffering from, a disease or condition which would be susceptible to treatment with a compound having activity against protein kinase A.

The use of a composition or compound of formula (I), or a salt, solvate, tautomer or N-oxide thereof as defined herein for the manufacture of a medicament for the treatment or prophylaxis of a disease state or condition in a patient who has been screened and has been determined as suffering from, or being at risk of suffering from, a disease or condition which would be susceptible to treatment with a compound having activity against protein kinase A.

A composition or compound of formula (I), or a salt, solvate, tautomer or N-oxide thereof as defined herein for use as a modulator (e.g. inhibitor) of protein kinase B and/or protein kinase A.

The use of a composition or compound of formula (I), or a salt, solvate, tautomer or N-oxide thereof as defined herein for the manufacture of a medicament for modulating (e.g. inhibiting) protein kinase B and/or protein kinase A.

A method of modulating (e.g. inhibiting) protein kinase B and/or protein kinase A; which method comprises bringing the protein kinase B and/or protein kinase A (e.g. in a cellular environment—for example in vivo) into contact with a composition or compound of formula (I), or a salt, solvate, tautomer or N-oxide thereof as defined herein.

A composition or compound of formula (I), or a salt, solvate, tautomer or N-oxide thereof as defined herein for use in: (a) the treatment or prophylaxis of a disease or condition in which the modulation (e.g. inhibition) of ROCK kinase is indicated; and/or (b) the treatment of a subject or patient population in which the modulation (e.g. inhibition) of ROCK kinase is indicated.

The use of a composition or compound of formula (I), or a salt, solvate, tautomer or N-oxide thereof as defined herein for the manufacture of a medicament for use in: (a) the treatment or prophylaxis of a disease or condition in which the modulation (e.g. inhibition) of ROCK kinase is indicated; and/or (b) the treatment of a subject or patient population in which the modulation (e.g. inhibition) of ROCK kinase is indicated.

A method for the prophylaxis or treatment of a disease state or condition mediated by ROCK kinase, which method comprises administering to a subject in need thereof a composition or compound of formula (I), or a salt, solvate, tautomer or N-oxide thereof as defined herein.

A method for treating a disease or condition comprising or arising from abnormal cell growth or abnormally arrested cell death in a mammal, the method comprising administering to the mammal a composition or compound of formula (I), or a salt, solvate, tautomer or N-oxide thereof as defined herein in an amount effective to inhibit ROCK kinase activity.

A method of inhibiting ROCK kinase, which method comprises contacting the kinase with a kinase-inhibiting composition or compound as defined herein.

A method of modulating a cellular process (for example cell division) by inhibiting the activity of a ROCK kinase using a composition or compound of formula (I), or a salt, solvate, tautomer or N-oxide thereof as defined herein.

A composition or compound of formula (I), or a salt, solvate, tautomer or N-oxide thereof as defined herein for use in the prophylaxis or treatment of a disease state or condition mediated by ROCK kinase.

The use of a composition or compound of formula (I), or a salt, solvate, tautomer or N-oxide thereof as defined herein for the manufacture of a medicament for the prophylaxis or treatment of a disease state or condition mediated by ROCK kinase.

The use of a composition or compound of formula (I), or a salt, solvate, tautomer or N-oxide thereof as defined herein for the manufacture of a medicament for the prophylaxis or treatment of a disease state or condition arising from abnormal cell growth or abnormally arrested cell death mediated by ROCK kinase.

A method for alleviating or reducing the incidence of a disease or condition comprising or arising from abnormal cell growth or abnormally arrested cell death in a mammal mediated by ROCK kinase, which method comprises administering to the mammal a composition or compound of formula (I), or a salt, solvate, tautomer or N-oxide thereof as defined herein in an amount effective in inhibiting abnormal cell growth.

The use of a composition or compound of formula (I), or a salt, solvate, tautomer or N-oxide thereof as defined herein for the manufacture of a medicament for the prophylaxis or treatment of any one of the disease states or conditions disclosed herein.

A method for the treatment or prophylaxis of any one of the disease states or conditions disclosed herein, which method comprises administering to a patient (e.g. a patient in need thereof) a composition or compound (e.g. a therapeutically effective amount) of formula (I) as defined herein.

A method for alleviating or reducing the incidence of a disease state or condition disclosed herein, which method comprises administering to a patient (e.g. a patient in need thereof) a composition or compound (e.g. a therapeutically effective amount) of formula (I) as defined herein.

A method for the diagnosis and treatment of a disease state or condition mediated by ROCK kinase, which method comprises (i) screening a patient to determine whether a disease or condition from which the patient is or may be suffering is one which would be susceptible to treatment with a compound having activity against ROCK kinase; and (ii) where it is indicated that the disease or condition from which the patient is thus susceptible, thereafter administering to the patient a composition or compound of formula (I), or a salt, solvate, tautomer or N-oxide thereof as defined herein.

The use of a composition or compound of formula (I), or a salt, solvate, tautomer or N-oxide thereof as defined herein for the manufacture of a medicament for the treatment or prophylaxis of a disease state or condition in a patient who has been screened and has been determined as suffering from, or being at risk of suffering from, a disease or condition which would be susceptible to treatment with a compound having activity against ROCK kinase.

A composition or compound of formula (I), or a salt, solvate, tautomer or N-oxide thereof as defined herein for use in: (a) the treatment or prophylaxis of a disease or condition in which the modulation (e.g. inhibition) of protein kinase p70S6K is indicated; and/or (b) the treatment of a subject or patient population in which the modulation (e.g. inhibition) of protein kinase p70S6K is indicated.

The use of a composition or compound of formula (I), or a salt, solvate, tautomer or N-oxide thereof as defined herein for the manufacture of a medicament for use in: (a) the treatment or prophylaxis of a disease or condition in which the modulation (e.g. inhibition) of protein kinase p70S6K is indicated; and/or (b) the treatment of a subject or patient population in which the modulation (e.g. inhibition) of protein kinase p70S6K is indicated.

A method for the prophylaxis or treatment of a disease state or condition mediated by protein kinase p70S6K, which method comprises administering to a subject in need thereof a composition or compound of the formula (I), or a salt, solvate, tautomer or N-oxide thereof as defined herein.

A method for treating a disease or condition comprising or arising from abnormal cell growth or abnormally arrested cell death in a mammal, the method comprising administering to the mammal a composition or compound of the formula (I), or a salt, solvate, tautomer or N-oxide thereof as defined herein in an amount effective to inhibit protein kinase p70S6K activity.

A method of inhibiting protein kinase p70S6K, which method comprises contacting the kinase with a kinase-inhibiting composition or compound of the formula (I), or a salt, solvate, tautomer or N-oxide thereof as defined herein.

A method of modulating a cellular process (for example cell division) by inhibiting the activity of protein kinase p70S6K using a composition or compound of the formula (I), or a salt, solvate, tautomer or N-oxide thereof as defined herein.

A composition or compound of the formula (I), or a salt, solvate, tautomer or N-oxide thereof as defined herein for use in the prophylaxis or treatment of a disease state or condition mediated by protein kinase p70S6K.

The use of a composition or compound of formula (I), or a salt, solvate, tautomer or N-oxide thereof as defined herein for the manufacture of a medicament for the prophylaxis or treatment of a disease state or condition mediated by protein kinase p70S6K.

The use of a composition or compound of the formula (I), or a salt, solvate, tautomer or N-oxide thereof as defined herein for the manufacture of a medicament for the prophylaxis or treatment of a disease state or condition arising from abnormal cell growth or abnormally arrested cell death mediated by protein kinase p70S6K.

A method for alleviating or reducing the incidence of a disease or condition comprising or arising from abnormal cell growth or abnormally arrested cell death in a mammal mediated by protein kinase p70S6K, which method comprises administering to the mammal a composition or compound of the formula (I), or a salt, solvate, tautomer or N-oxide thereof as defined herein in an amount effective in inhibiting abnormal cell growth.

The use of a composition or compound of the formula (I), or a salt, solvate, tautomer or N-oxide thereof as defined herein for the manufacture of a medicament for the prophylaxis or treatment of any one of the disease states or conditions disclosed herein.

A method for the treatment or prophylaxis of any one of the disease states or conditions disclosed herein, which method comprises administering to a patient (e.g. a patient in need thereof) a composition or compound (e.g. a therapeutically effective amount) of the formula (I) as defined herein.

A method for alleviating or reducing the incidence of a disease state or condition disclosed herein, which method comprises administering to a patient (e.g. a patient in need thereof) a composition or compound (e.g. a therapeutically effective amount) of the formula (I) as defined herein.

A method for the diagnosis and treatment of a disease state or condition mediated by protein kinase p70S6K, which method comprises (i) screening a patient to determine whether a disease or condition from which the patient is or may be suffering is one which would be susceptible to treatment with a compound having activity against protein kinase p70S6K; and (ii) where it is indicated that the disease or condition from which the patient is thus susceptible, thereafter administering to the patient a composition or compound of the formula (I), or a salt, solvate, tautomer or N-oxide thereof as defined herein.

The use of a composition or compound of the formula (I), or a salt, solvate, tautomer or N-oxide thereof as defined herein for the manufacture of a medicament for the treatment or prophylaxis of a disease state or condition in a patient who has been screened and has been determined as suffering from, or being at risk of suffering from, a disease or condition which would be susceptible to treatment with a compound having activity against protein kinase p70S6K.

The invention also provides the further combinations, uses, methods, compounds and processes as set out in the claims below.

General Preferences and Definitions

As used herein, the term "modulation", as applied to the activity of a kinase, is intended to define a change in the level of biological activity of the protein kinase. Thus, modulation encompasses physiological changes which effect an increase or decrease in the relevant protein kinase activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of kinase activity. Thus, modulation may imply elevated/suppressed expression or over- or under-expression of a kinase, including gene amplification (i.e. multiple gene copies) and/or increased or decreased expression by a transcriptional effect, as well as hyper-(or hypo-)activity and (de)activation of the protein kinase(s) (including (de)activation) by mutation(s). The terms "modulated", "modulating" and "modulate" are to be interpreted accordingly.

As used herein, the term "mediated", as used e.g. in conjunction with a kinase as described herein (and applied for example to various physiological processes, diseases, states, conditions, therapies, treatments or interventions) is intended to operate limitatively so that the various processes, diseases, states, conditions, treatments and interventions to which the term is applied are those in which the kinase plays a biological role. In cases where the term is applied to a disease, state or condition, the biological role played by a kinase may be direct or indirect and may be necessary and/or sufficient for the manifestation of the symptoms of the disease, state or condition (or its aetiology or progression). Thus, kinase activity (and in particular aberrant levels of kinase activity, e.g. kinase over-expression) need not necessarily be the proximal cause of the disease, state or condition: rather, it is contemplated that the kinase mediated diseases, states or conditions include those having multifactorial aetiologies and complex progressions in which the kinase in question is only partially involved. In cases where the term is applied to treatment, prophylaxis or intervention, the role played by the kinase may be direct or indirect and may be necessary and/or sufficient for the operation of the treatment, prophylaxis or outcome of the intervention. Thus, a disease state or condition mediated by a kinase includes the development of resistance to any particular cancer drug or treatment.

As used herein, the terms "ROCK kinase(s)" and "ROCK(s)" are synonomous generic terms embracing all members of the ROCK kinase family, so including both ROCK1 and ROCK2 as species within the genus. References inter alia to ROCK kinase inhibitors, ROCK kinase modulation and ROCK kinase activity are to be interpreted accordingly.

The term "Rho protein" is a term of art used to define a large family of GTP-binding proteins that are involved in regulation of actin organization, including RhoA and RhoC.

As used herein, the term "Rho signalling pathway" defines any cellular signaling pathway in which one or more members of the Rho proteins are involved. Particularly relevant to the invention are Rho signaling pathways in which a ROCK kinase (e.g. ROCK1 and/or ROCK2) is a proximate effector (e.g. a binding partner) for one or more Rho protein(s), and such Rho signaling pathways are preferred in embodiments of the invention defined inter alia by reference to a Rho signaling pathway.

As used herein, the term "modulation", as applied to the ROCKs as described herein, is intended to define a change in the level of biological activity of the ROCKs. Thus, modulation encompasses physiological changes which effect an increase or decrease in ROCK activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of ROCK activity, or at the level of enzyme (e.g. ROCK) activity (for example by allosteric mechanisms, competitive inhibition, active-site inactivation, perturbation of feedback inhibitory pathways etc.). Thus, modulation may imply elevated/suppressed expression or over- or under-expression of the ROCK, including gene amplification (i.e. multiple gene copies) and/or increased or decreased expression by a transcriptional effect, as well as hyper-(or hypo-) activity and (de)activation of the ROCK (including (de)activation) by mutation(s). The terms "modulated" and "modulate" are to be interpreted accordingly.

As used herein, the term "mediated", as used in conjunction with the ROCKs as described herein (and applied for example to various physiological processes, diseases, states, conditions, therapies, treatments or interventions) is intended to operate limitatively so that the various processes, diseases, states, conditions, treatments and interventions to which the term is applied are those in which ROCK plays a biological role. In cases where the term is applied to a disease, state or condition, the role played by ROCK may be direct or indirect and may be necessary and/or sufficient for the manifestation of the symptoms of the disease, state or condition (or its aetiology or progression). Thus, ROCK activity (and in particular aberrant levels of ROCK activity, e.g. ROCK over-expression) need not necessarily be the proximal cause of the disease, state or condition: rather, it is contemplated that ROCK-mediated diseases, states or conditions include those having multifactorial aetiologies and complex progressions in which ROCK is only partially involved. In cases where the term is applied to treatment, prophylaxis or intervention (e.g. in the "ROCK-mediated treatments" and "ROCK-mediated prophylaxis" of the invention), the role played by ROCK may be direct or indirect and may be necessary and/or sufficient for the operation of the treatment, prophylaxis or outcome of the intervention. Many ROCK-mediated physiological processes, diseases, states, conditions, therapies, treatments or interventions of the invention involve the Rho signaling pathway (as herein defined) and may therefore, by extension, be dubbed "Rho-mediated" physiological processes, diseases, states, conditions, therapies, treatments or interventions.

The term "indicated" is a term of art used herein in relation to a disease, condition, subject or patient population to convey the clinical desirability or necessity of a particular intervention in relation to that disease, condition, subject or patient population. Thus, references herein to a disease, condition, subject or patient population "in which the modulation (e.g. inhibition) of ROCK kinase is indicated" is intended to define those diseases etc. in which modulation of ROCK kinase is either clinically desirable or necessary. This might be the case, for example, where modulation of ROCK kinase would be palliative, preventative or (at least partially) curative.

As used herein, the term "modulation", as applied to the protein kinase P70S6K described herein, is intended to define a change in the level of biological activity of P70S6K. Thus, modulation encompasses physiological changes which effect an increase or decrease in P70S6K activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of P70S6K activity, or at the level of enzyme (e.g. P70S6K) activity (for example by allosteric mechanisms, competitive inhibition, active-site inactivation, perturbation of feedback inhibitory pathways etc.). Thus, modulation may imply elevated/suppressed expression or over- or under-expression of P70S6K, including gene amplification (i.e. multiple gene copies) and/or increased or decreased expression by a transcriptional effect, as well as hyper-(or hypo-)activity and (de)activation of P70S6K (including (de)activation) by mutation(s). The terms "modulated" and "modulate" are to be interpreted accordingly.

As used herein, the term "mediated", as used in conjunction with P70S6K as described herein (and applied for example to various physiological processes, diseases, states, conditions, therapies, treatments or interventions) is intended to operate limitatively so that the various processes, diseases, states, conditions, treatments and interventions to which the term is applied are those in which P70S6K plays a biological role. In cases where the term is applied to a disease, state or condition, the role played by P70S6K may be direct or indirect and may be necessary and/or sufficient for the manifestation of the symptoms of the disease, state or condition (or its aetiology or progression). Thus, P70S6K activity (and in particular aberrant levels of P70S6K activity, e.g. P70S6K over-expression) need not necessarily be the proximal cause of the disease, state or condition: rather, it is contemplated that P70S6K-mediated diseases, states or conditions include those having multifactorial aetiologies and complex progressions in which P70S6K is only partially involved. In cases where the term is applied to treatment, prophylaxis or intervention (e.g. in the "P70S6K-mediated treatments" and "P70S6K-mediated prophylaxis" of the invention), the role played by P70S6K may be direct or indirect and may be necessary and/or sufficient for the operation of the treatment, prophylaxis or outcome of the intervention.

The term "intervention" is a term of art used herein to define any agency which effects a physiological change at any level. Thus, the intervention may comprise the induction or repression of any physiological process, event, biochemical pathway or cellular/biochemical event. The interventions of the invention typically effect (or contribute to) the therapy, treatment or prophylaxis of a disease or condition.

Unless the context indicates otherwise, references herein to (S)-2-amino-1-(4-chloro-phenyl)-1-[4-(1H-pyrazol-4-yl)-phenyl]-ethanol, or the compound of formula (I) or the S-enantiomer include the free base as well as ionic, salt, solvate, N-oxide, tautomeric and protected forms thereof, for example, as discussed below.

The compound may be other than an N-oxide. For example, in one embodiment, the compound of formula (I) is other than an N-oxide and is in the form of a free base.

In another embodiment, the compound of formula (I) is other than an N-oxide and is in the form of a salt.

Salt forms may be selected and prepared according to methods described in *Pharmaceutical Salts Properties, Selection, and Use*, P. Heinrich Stahl (Editor), Camille G. Wermuth (Editor), ISBN: 3-90639-026-8, Hardcover, 388 pages, August 2002. For example, acid addition salts may be prepared by dissolving the free base in an organic solvent in which a given salt form is insoluble or poorly soluble and then adding the required acid in an appropriate solvent so that the salt precipitates out of solution.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethane-sulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic, (−)-L-malic, malonic, (±)-DL-mandelic, methanesulphonic, naphthalenesulphonic (e.g. naphthalene-2-sulphonic), naphthalene-1,5-disulphonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulphuric, tannic, (+)-L-tartaric, thiocyanic, toluenesulphonic (e.g. p-toluenesulphonic), undecylenic and valeric acids, as well as acylated amino acids and cation exchange resins.

One particular group of acid addition salts includes salts formed with hydrochloric, hydriodic, phosphoric, nitric, sulphuric, citric, lactic, succinic, maleic, malic, isethionic, fumaric, benzenesulphonic, toluenesulphonic, methanesulphonic, ethanesulphonic, naphthalenesulphonic, valeric, acetic, propanoic, butanoic, malonic, glucuronic and lactobionic acids. Within this group of salts, a sub-set of salts consists of salts formed with hydrochloric acid or acetic acid.

Another group of acid addition salts includes salts formed from acetic, adipic, ascorbic, aspartic, citric, DL-Lactic, fumaric, gluconic, glucuronic, hippuric, hydrochloric, glutamic, DL-malic, methanesulphonic, sebacic, stearic, succinic and tartaric acids.

The compound of formula (I) may exist as mono- or di-salts depending upon the pKa of the acid from which the salt is formed. In stronger acids, the basic pyrazole nitrogen, as well as the nitrogen atom in the amino group, may take part in salt formation. For example, where the acid has a pKa of less than about 3 (e.g. an acid such as hydrochloric acid, sulphuric acid or trifluoroacetic acid), the compound of formula (I) will typically form salts with 2 molar equivalents of the acid.

The salt forms of the compound of formula (I) are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts.

Such non-pharmaceutically acceptable salts forms, which may be useful, for example, in the purification or separation of the compound of formula (I), also form part of the invention.

The compound of formula (I) may also form N-oxides and such N-oxides are within the scope of the definition of the compound of formula (I).

In one general embodiment, the compound of formula (I) is not an N-oxide.

N-Oxides can be formed by treatment of the parent amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

The compound of formula (I) can be prepared from a racemic mixture of the S-enantiomer and the R-enantiomer by using a suitable separation technique such as chiral chromatography (chromatography on a chiral support) and such techniques are well known to the person skilled in the art.

As an alternative to chiral chromatography, the enantiomers can be separated by forming diastereoisomeric salts with chiral acids such as (+)-tartaric acid, (−)-pyroglutamic acid, (−)-di-toluloyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

The compound of formula (I) includes variants with one or more isotopic substitutions, and a reference to a particular element includes within its scope all isotopes of the element. For example, a reference to hydrogen includes within its scope $^1$H, $^2$H (D), and $^3$H (T). Similarly, references to carbon and oxygen include within their scope respectively $^{12}$C, $^{13}$C and $^{14}$C and $^{16}$O and $^{18}$O.

The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Also encompassed by formula (I) are any polymorphic forms of the compounds, solvates (e.g. hydrates), complexes (e.g. inclusion complexes or clathrates with compounds such as cyclodextrins, or complexes with metals) of the compounds, and pro-drugs of the compounds. By "prodrugs" is meant for example any compound that is converted in vivo into a biologically active composition as defined herein.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the hydroxyl groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:

$C_{1-7}$alkyl
(e.g., -Me, -Et, -nPr, -iPr, -nBu, -sBu, -iBu, -tBu);

$C_{1-7}$aminoalkyl
(e.g., aminoethyl; 2-(N,N-diethylamino)ethyl; 2-(4-morpholino)ethyl); and acyloxy-$C_{1-7}$alkyl
(e.g., acyloxymethyl;

acyloxyethyl;

pivaloyloxymethyl;

acetoxymethyl;

1-acetoxyethyl;

1-(1-methoxy-1-methyl)ethyl-carbonxyloxyethyl;

1-(benzoyloxy)ethyl; isopropoxy-carbonyloxymethyl;

1-isopropoxy-carbonyloxyethyl; cyclohexyl-carbonyloxymethyl;

1-cyclohexyl-carbonyloxyethyl;

cyclohexyloxy-carbonyloxymethyl;

1-cyclohexyloxy-carbonyloxyethyl;

(4-tetrahydropyranyloxy) carbonyloxymethyl;

1-(4-tetrahydropyranyloxy)carbonyloxyethyl;

(4-tetrahydropyranyl)carbonyloxymethyl; and 1-(4-tetrahydropyranyl)carbonyloxyethyl).

Also, some prodrugs are activated enzymatically to yield the active compound, or a compound which, upon further chemical reaction, yields the active compound (for example, as in Antibody-directed Enzyme Prodrug Therapy (ADEPT), Gene-directed Enzyme Prodrug Therapy (GDEPT), Polymer-directed Enzyme Prodrug Therapy (PDEPT), Ligand-directed Enzyme Prodrug Therapy (LIDEPT), etc.). For example, the prodrug may be a sugar derivative or other glycoside conjugate, or may be an amino acid ester derivative.

Synthetic Methods

The compound of the formula (I) and its R-enantiomer and mixtures thereof can be prepared by the methods shown in Scheme 1.

In Scheme 1, the substituted benzophenone (10) is converted to the epoxide (11) by reaction with trimethylsulphonium iodide in dimethylsulphoxide in the presence of a base (e.g. a hydride base such as sodium hydride). The epoxide (11) is then reacted with ammonia in an alcoholic solvent such as methanol, typically with heating, to give the amine (12) as a racemic mixture of R- and S-enantiomers.

The amine (12) can be reacted directly with a pyrazole boronate (such as 4-(4,4,5,5-tetramethyl-[1,3,2]dioxaborolan-2-yl)-1H-pyrazole) in the presence of a palladium catalyst (such as tetrakistriphenylphosphine palladium (0)) under Suzuki coupling conditions to give the racemic compound (15). However, it has been found that reacting the unprotected amine under Suzuki coupling conditions gives relatively poor product yields and the product is relatively difficult to purify because of its low solubility. This problem is overcome by first protecting the amino group (e.g. with a Boc group whereby PG=Boc) to give the protected intermediate (13) and then subjecting intermediate (13) to Suzuki coupling to give the protected compound (14). The protected compound (14) is then deprotected by well known methods (e.g. using HCl in ether/methanol when PG=Boc) to give the product (15) as a racemic mixture.

Scheme 1

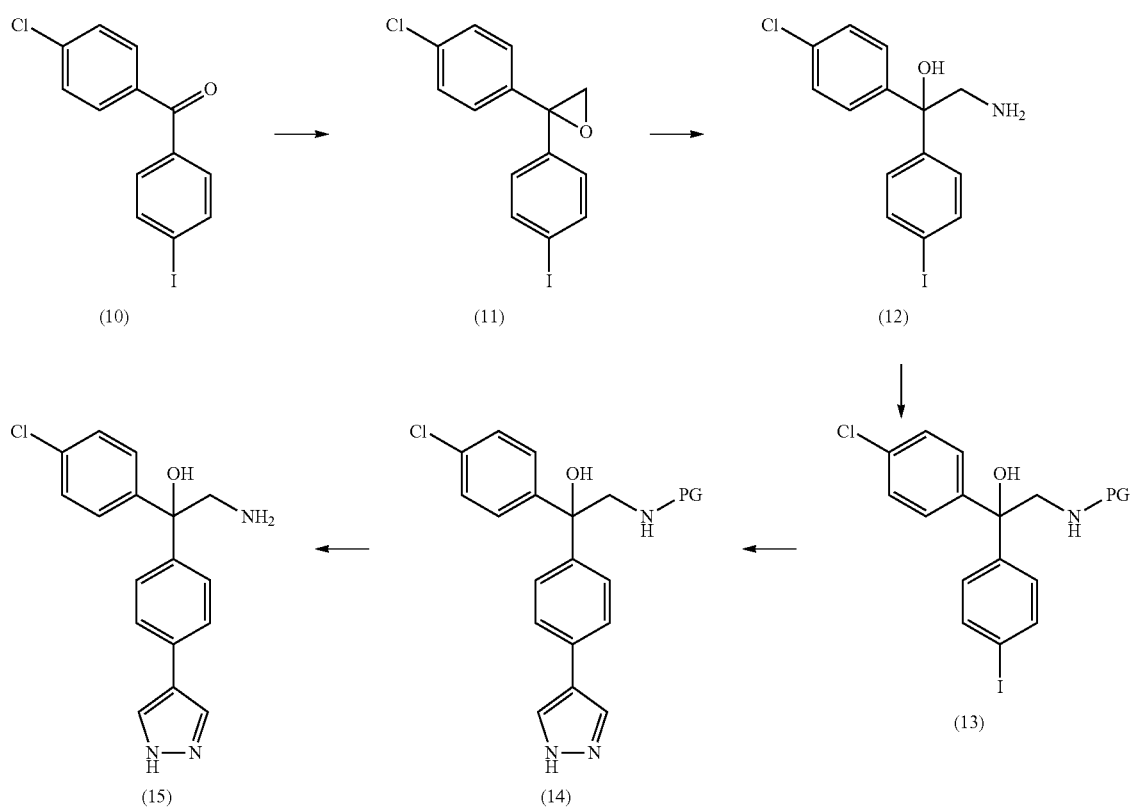

The racemic mixture (15) can be resolved by methods well known to those skilled in the art, for example using the chiral chromatography methods and other methods described herein.

In another aspect, the invention provides a process for the preparation of a compound of the formula (15), which process comprises the removal of a protecting group PG from a compound of the compound (14) and thereafter optionally separating the optical isomers of compound (15) and isolating the S-enantiomer thereof. The invention also provides a compound preparable by the foregoing process, as well as a compound of the formula (15) whenever prepared by the said process.

In a further aspect, the invention provides a process for the preparation of a compound of the formula (15), which process comprises (i) reacting a compound of the formula (13) with a pyrazole derivative of the formula (16):

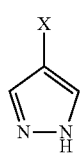
(16)

wherein X is a group B(OH)$_2$ or a boronate ester group (such as a 4,4,5,5-tetramethyl-[1,3,2]dioxaborolan-2-yl group) in the presence of a palladium catalyst (such as tetrakistriphenylphosphine palladium (0)) under Suzuki coupling conditions to give a compound of the formula (14); (ii) removing the protecting group PG from the compound of the compound (14) and thereafter (iii) optionally separating the optical isomers of compound (15) and isolating the S-enantiomer thereof.

Intermediates of the formula (13), particularly wherein PG is a Boc group, constitute a further aspect of the invention.

Novel intermediates of the formula (14), wherein PG is other than a 2-carboxy-benzoyl group, also form a further aspect of the invention. A preferred intermediate (14) is the compound wherein PG is a Boc group.

As an alternative to the methods described above and illustrated in Scheme 1, the compound of formula (I) can be prepared by following the method described in Example 84 of WO 2005/061463 (Astex) and then isolating the S-enantiomer using the separation methods described above and elsewhere herein.

An improved process for making the intermediate compound (12) is illustrated in Scheme 2.

Scheme 2

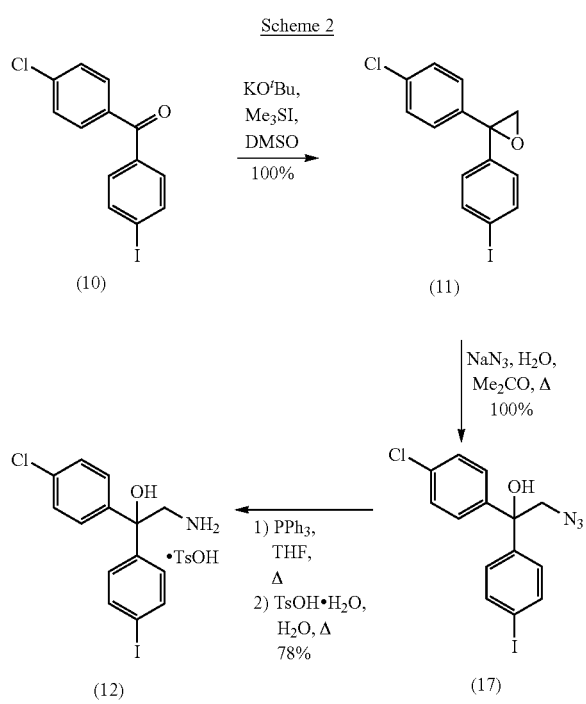

In Scheme 2, the substituted benzophenone (10) is converted to the epoxide (11) by reaction with trimethylsulphonium iodide in dimethylsulphoxide in the presence of a base as described in Scheme 1 above, except that the sodium hydride base is replaced with potassium tert-butoxide. The potassium tert-butoxide is added to a rapidly stirred mixture of the benzophenone (10) and trimethylsulphonium iodide, typically at room temperature. The use of potassium tert-butoxide as the base rather than sodium hydride confers significant advantages. Firstly, rather than forming the dimsyl anion by reaction of base with DMSO and then adding the other reactants, as is the case when sodium hydride is used as the base, the tert-butoxide can be added to a preformed mixture of the benzophenone (10), trimethylsulphonium iodide and dimethylsulphoxide. This means that the dimsyl anion is consumed very quickly after it is formed and therefore only small amounts of the dimsyl anion are present in the reaction mixture at any given time. Thus the use of potassium tert-butoxide avoids the formation of large concentrations of the relatively viscous and somewhat hazardous dimsyl sodium. In addition to improving the safety of the process, the absence of large concentrations of the viscous dimsyl sodium means that the reaction mixture is much easier to stir allowing more efficient mixing of the reactants and the avoidance of localised pockets of unreacted or incompletely reacted materials, an advantage which is enhanced by the fact that the tert-butanol formed during the reaction is a good solvent for the reactants and product. These benefits are particularly apparent when the reaction is carried out on a larger scale (e.g. to prepare quantities of 50 grammes or more of the epoxide (11) where it has been found that the use of potassium tert-butoxide gives rise to substantially better yields of the epoxide (11) and better purity (compared to reactions using sodium hydride as the base).

In the reaction sequence shown in Scheme 1, the epoxide (11) is reacted with ammonia in an alcoholic solvent such as methanol with heating, to give the amine (12). Reactions of this type may be carried out in a microwave reactor, typically under pressure and give good yields and purity on relatively small scale reactions.

However, for larger scale reactions (e.g. for producing quantities of 50 grammes or more of the amine (12)), it has been found that reacting the epoxide (11) with sodium azide and then reducing the azide intermediate (17) to the amine (12) gives better yields and greater purity. The reaction of the epoxide (11) with the sodium azide is typically carried out in a polar solvent, e.g. an aqueous solvent comprising water and a water-miscible solvent such as acetone. The reaction is usually carried out with heating, for example to the reflux temperature of the solvent system.

Conversion of the azido alcohol (17) to the amino alcohol (12) may be achieved by reaction with triphenyl phosphine followed by treatment with an aqueous acid and particularly an aqueous solution of a substituted sulphonic acid, preferably an alkyl- or arylsulphonic acid such as methanesulphonic acid, ethanesulphonic acid, benzenesulphonic acid, toluenesulphonic acid or camphorsulphonic acid. The use of 4-toluenesulphonic acid is particularly preferred. Without wishing to be bound by any theory, the reaction is believed to proceed by initial cyclisation to form an aziridine followed by ring opening in the presence of the acid to give the amino alcohol. By using an acid (particularly 4-toluenesulphonic acid), the amino-alcohol can be isolated as a stable, easy to handle salt and readily purified. If an optically active form of camphorsulphonic acid (e.g. d-camphorsulphonic acid) is used, fractional crystallisation of the salt can be carried out to separate the individual salts of the two enantiomers of the amino alcohol (12). Treatment of the salts with base then gives the individual enantiomers of the amino alcohol (12).

The azide compound (17), the amino-alcohol (12) and its individual enantiomers and acid addition salts of the amino-alcohol (12) and its enantiomers are believed to be novel and, as such, form further aspects of the invention.

Thus, in one embodiment, the invention provides 2-amino-1-(4-chloro-phenyl)-1-[4-iodo-phenyl]-ethanol and acid addition salts thereof as defined herein.

In another embodiment, the invention provides (R)2-amino-1-(4-chloro-phenyl)-1-[4-iodo-phenyl]-ethanol, and acid addition salts thereof as defined herein.

In a further embodiment, the invention provides (S)2-amino-1-(4-chloro-phenyl)-1-[4-iodo-phenyl]-ethanol, and acid addition salts thereof as defined herein.

In each of the foregoing three embodiments, preferred acid addition salts are salts formed with methanesulphonic acid, ethanesulphonic acid, benzenesulphonic acid, toluenesulphonic acid or camphorsulphonic acid (e.g. d-camphorsulphonic acid). A particularly preferred salt is the salt formed with 4-toluenesulphonic acid.

In addition to being useful as a synthetic intermediate, the compound of the formula (12) and its acid addition salts have activity against the kinase PKB and, as such, should be useful in therapy, and in particular for the uses (e.g. anti-cancer uses) described herein for the compound of formula (I). Pharmaceutical compositions containing the compound of formula (12) or an acid addition salt thereof as defined herein and a pharmaceutically acceptable carrier, and the therapeutic uses of the compound of formula (12) or its acid addition salts constitute further aspects of the invention.

In another aspect, the invention provides a method of preparing an optically active form of a compound of the formula (12), which method comprises the fractional crystallisation of an acid addition salt of the compound of the formula (12), wherein the salt is derived from an optically active acid (e.g. d-camphorsulphonic acid).

In another aspect, the invention provides a process for the preparation of a compound of the formula (12) as defined herein, which process comprises the reaction of a compound of the formula (17) with a tertiary phosphine such as triphenylphosphine in a polar aprotic solvent such as tetrahydrofuran at a temperature above room temperature (for example at the reflux temperature of the solvent) followed by treatment with aqueous acid, for example a substituted sulphonic acid such as 4-toluenesulphonic acid.

As an alternative to triphenylphosphine, other tertiary phosphines may be used and these include other triarylphosphines such as tritolylphosphine, trialkylphosphines such as tributylphosphine, tri-cycloalkyl phosphines such as tricyclohexylphosphine, and tertiary phosphines containing mixtures of aryl and/or alkyl and/or cycloalkyl groups. However, triphenylphosphine is preferred.

As an alternative to 4-toluenesulphonic acid, other substituted sulphonic acids may be used; for example alkyl- and arylsulphonic acid such as methanesulphonic acid, ethanesulphonic acid, benzenesulphonic acid, and camphorsulphonic acid, as described above.

In another aspect the invention provides a process for the preparation of a compound of the formula (17); which process comprises the reaction of an epoxide compound of the formula (11) with an alkali metal azide (e.g. sodium azide) or trimethylsilylazide (TMS-azide) in a polar solvent (e.g. an aqueous organic solvent such as aqueous acetone), preferably with heating (for example to the reflux temperature of the solvent).

In a further aspect, the invention provides a process for the preparation of a compound of the formula (12), which process comprises the steps of:

(a) the reaction of a compound of the formula (11) as defined herein with an alkali metal azide (such as sodium azide) or trimethylsilyl azide to form a compound of the formula (17);

(b) the reaction of the compound of the formula (17) with (i) a tertiary phosphine such as triphenylphosphine, followed by (ii) an acid such as example a substituted sulphonic acid, preferably an alkyl- or arylsulphonic acid such as methanesulphonic acid, ethanesulphonic acid, benzenesulphonic acid or toluenesulphonic acid, and most preferably 4-toluenesulphonic acid.

In each of the above processes involving the use of an azide, alkali metal azides (e.g. lithium azide, potassium azide and sodium azide) are preferred and sodium azide is most preferred.

In another aspect, the invention provides a process for the preparation of a compound of the formula (15), 2-amino-1-(4-chloro-phenyl)-1-[4-(1H-pyrazol-4-yl)-phenyl]-ethanol; which method comprises:

(1) preparing a compound of the formula (12) by a method as defined herein;

(2) protecting the amino group of the compound of formula (12) by a method as defined herein to give a compound of formula (13);

(3) reacting a compound of the formula (13) with a pyrazole derivative of the formula (16) as defined herein in the presence of a palladium catalyst (such as tetrakistriphenylphosphine palladium (0)) under Suzuki coupling conditions to give a compound of the formula (14);

(4) removing the protecting group PG from the compound of the formula (14); and optionally thereafter (5) separating the optical isomers of compound (15) and isolating the S-enantiomer thereof.

Pharmaceutical Formulations

While it is possible for the compound of formula (I) to be administered alone, it is preferred that the composition of the invention is a pharmaceutical composition (e.g. formulation) comprising a compound of formula (I) together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

Thus, the present invention further provides pharmaceutical compositions, as defined above, and methods of making a pharmaceutical composition comprising admixing the compound of formula (I) together with one or more pharmaceutically acceptable carriers, excipients, buffers, adjuvants, stabilizers, or other materials, as described herein.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Pharmaceutical compositions containing the composition as defined herein can be formulated in accordance with known techniques, see for example, Remington's Pharmaceutical Sciences, Mack Publishing Company, Easton, Pa., USA.

Accordingly, in a further aspect, the invention provides the composition as defined herein in the form of a pharmaceutical composition.

The pharmaceutical compositions can be in any form suitable for oral, parenteral, topical, intranasal, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump.

Pharmaceutical formulations adapted for parenteral administration include aqueous and non-aqueous sterile injection solutions which may contain anti-oxidants, buffers, bacteriostats, co-solvents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

Liposomes are closed spherical vesicles composed of outer lipid bilayer membranes and an inner aqueous core and with an overall diameter of <100 μm. Depending on the level of hydrophobicity, moderately hydrophobic drugs can be solubilized by liposomes if the drug becomes encapsulated or intercalated within the liposome. Hydrophobic drugs can also be solubilized by liposomes if the drug molecule becomes an integral part of the lipid bilayer membrane, and in this case, the hydrophobic drug is dissolved in the lipid portion of the lipid bilayer.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use.

The pharmaceutical formulation can be prepared by lyophilising a compound of formula (I). Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In one preferred embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another preferred embodiment, the pharmaceutical composition is in a form suitable for sub-cutaneous (s.c.) administration.

Pharmaceutical dosage forms suitable for oral administration include tablets, capsules, caplets, pills, lozenges, syrups, solutions, powders, granules, elixirs and suspensions, sublingual tablets, wafers or patches and buccal patches.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated, but typically have a coating, for example a protective film coating (e.g. a wax or varnish) or a release controlling coating. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum or duodenum.

Instead of, or in addition to, a coating, the drug can be presented in a solid matrix comprising a release controlling agent, for example a release delaying agent which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. As a further alternative, the active compound can be formulated in a delivery system that provides osmotic control of the release of the compound. Osmotic release and other delayed release or sustained release formulations may be prepared in accordance with methods well known to those skilled in the art.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragées, tablets or capsules.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into plastics carriers that allow the active ingredients to diffuse or be released in measured amounts.

The compositions of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

This invention also provides solid dosage forms comprising the solid solution described above. Solid dosage forms include tablets, capsules and chewable tablets. Known excipients can be blended with the solid solution to provide the desired dosage form. For example, a capsule can contain the solid solution blended with (a) a disintegrant and a lubricant, or (b) a disintegrant, a lubricant and a surfactant. A tablet can contain the solid solution blended with at least one disintegrant, a lubricant, a surfactant, and a glidant. The chewable tablet can contain the solid solution blended with a bulking agent, a lubricant, and if desired an additional sweetening agent (such as an artificial sweetener), and suitable flavours.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compositions will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within this range, particular subranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 milligrams to 1 gram, of active compound.

The active compound will be administered to a patient in need thereof (for example a human or animal patient) in an amount sufficient to achieve the desired therapeutic effect.

Protein Kinase Inhibitory Activity

The activity of the compound of formula (I) as inhibitors of protein kinase A and protein kinase B can be measured using the assays set forth in the examples below and the level of activity exhibited by a given compound can be defined in terms of the $IC_{50}$ value.

Therapeutic Uses

Prevention or Treatment of Proliferative Disorders

The compound of the formula (I) is an inhibitor of protein kinase A and protein kinase B. As such, it will be useful in providing a means of preventing the growth of or inducing apoptosis of neoplasias. The compositions of the invention will therefore prove useful in treating or preventing proliferative disorders such as cancers. In particular tumours with deletions or inactivating mutations in PTEN or loss of PTEN expression or rearrangements in the (T-cell lytmphocyte) TCL-1 gene may be particularly sensitive to PKB inhibitors. Tumours which have other abnormalities leading to an upregulated PKB pathway signal may also be particularly sensitive to inhibitors of PKB. Examples of such abnormalities include but are not limited to overexpression of one or more PI3K subunits, over-expression of one or more PKB isoforms, or mutations in PI3K, PDK1, or PKB which lead to an increase in the basal activity of the enzyme in question, or upregulation or overexpression or mutational activation of a growth factor receptor such as a growth factor selected from the epidermal growth factor receptor (EGFR), fibroblast growth factor receptor (FGFR), platelet derived growth factor receptor (PDGFR), insulin-like growth factor 1 receptor (IGF-1R) and vascular endothelial growth factor receptor (VEGFR) families.

The compositions of the invention will also be useful in treating other conditions which result from disorders in proliferation or survival such as viral infections, and neurodegenerative diseases for example. PKB plays an important role in maintaining the survival of immune cells during an immune response and therefore PKB inhibitors could be particularly beneficial in immune disorders including autoimmune conditions.

Therefore, PKB inhibitors could be useful in the treatment of diseases in which there is a disorder of proliferation, apoptosis or differentiation.

PKB inhibitors may also be useful in diseases resulting from insulin resistance and insensitivity, and the disruption of glucose, energy and fat storage such as metabolic disease and obesity.

Examples of cancers which may be inhibited include, but are not limited to, a carcinoma, for example a carcinoma of the bladder, breast, colon (e.g. colorectal carcinomas such as colon adenocarcinoma and colon adenoma), kidney, epidermal, liver, lung, for example adenocarcinoma, small cell lung cancer and non-small cell lung carcinomas, oesophagus, gall bladder, ovary, pancreas e.g. exocrine pancreatic carcinoma, stomach, cervix, endometrium, thyroid, prostate, or skin, for example squamous cell carcinoma; a hematopoietic tumour of lymphoid lineage, for example leukaemia, acute lymphocytic leukaemia, B-cell lymphoma, multiple myeloma, T-cell lymphoma, Hodgkin's lymphoma, non-Hodgkin's lymphoma, hairy cell lymphoma, or Burkitt's lymphoma; a hematopoietic tumour of myeloid lineage, for example acute and chronic myelogenous leukaemias, myelodysplastic syndrome, or promyelocytic leukaemia; myeloproliferative syndrome; thyroid follicular cancer; a tumour of mesenchymal origin, for example fibrosarcoma or rhabdomyosarcoma; a tumour of the central or peripheral nervous system, for example astrocytoma, neuroblastoma, glioma or schwannoma; melanoma; seminoma; teratocarcinoma; osteosarcoma; xenoderoma pigmentosum; keratoctanthoma; thyroid follicular cancer; or Kaposi's sarcoma.

Thus, in the pharmaceutical compositions, uses or methods of this invention for treating a disease or condition comprising abnormal cell growth, the disease or condition comprising abnormal cell growth in one embodiment is a cancer.

Particular subsets of cancers include breast cancer, ovarian cancer, colon cancer, prostate cancer, oesophageal cancer, squamous cancer and non-small cell lung carcinomas.

A further subset of cancers includes breast cancer, ovarian cancer, prostate cancer, endometrial cancer and glioma.

The compositions of the invention can also be used in combination with other anticancer agents. Examples of such combinations are set out below.

Immune Disorders

Immune disorders for which the compositions of the invention may be beneficial include but are not limited to autoimmune conditions and chronic inflammatory diseases, for example systemic lupus erythematosus, autoimmune mediated glomerulonephritis, rheumatoid arthritis, psoriasis, inflammatory bowel disease, and autoimmune diabetes mellitus, Eczema hypersensitivity reactions, asthma, COPD, rhinitis, and upper respiratory tract disease.

Other Therapeutic Uses

PKB plays a role in apoptosis, proliferation, differentiation and therefore the compound of formula (I) could also be useful in the treatment of the following diseases other than cancer and those associated with immune dysfunction; viral infections, for example herpes virus, pox virus, Epstein-Barr virus, Sindbis virus, adenovirus, HIV, HPV, HCV and HCMV; prevention of AIDS development in HIV-infected individuals; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, degenerative diseases of the musculoskeletal system, for example, osteoporosis and arthritis, aspirin-sensitive rhinosinusitis, cystic fibrosis, multiple sclerosis, kidney diseases.

Uses Associated with or Arising from Rock Kinase Inhibitory Activity

The compounds of formula (I) modulate (e.g. inhibit) the activity of ROCK kinase. The compounds therefore find application in: (a) the treatment or prophylaxis of a disease or condition in which the modulation (e.g. inhibition) of ROCK kinase is indicated; and/or (b) the treatment of a subject or patient population in which the modulation (e.g. inhibition) of ROCK kinase is indicated; and/or (c) the treatment or prophylaxis of a disease or condition in which the modulation (e.g. inhibition) of the Rho signalling pathway is indicated; and/or (d) the treatment of a subject or patient population in which the modulation (e.g. inhibition) of the Rho signalling pathway is indicated.

The invention therefore finds application in relation to diseases and conditions selected from: (a) tumour metastasis; (b) tumour invasion; (c) tumour progression; (d) tumour adhesion (e.g. tumour cell adhesion); (e) actinomycin contractility-dependent tumour metastasis, invasion or progression; (f) cell transformation; (g) ROCK-mediated tumour metastasis, invasion, progression or adhesion; (h) ROCK-mediated actinomycin contractility-dependent tumour metastasis, invasion or progression; (i) ROCK-mediated cell transformation.

The invention also finds application in relation to cancer (e.g. ROCK-mediated cancer), especially where the cancer (for example being a ROCK-mediated cancer) is selected from: (a) testicular germ cell tumours; (b) small breast carcinomas with metastatic ability; (c) bladder cancer; (d) ovarian cancer; (e) prostate cancer; and (f) hepatocellular carcinoma.

Other applicable diseases and conditions include the invasion, metastasis and tumour progression of any of the cancers defined herein.

The invention also finds application in relation to cardiovascular diseases or conditions, particularly those selected from: (a) hypertension; (b) heart dysfunction (e.g. chronic and congestive heart failure); (c) cardiac hypertrophy; (d) restenosis; (e) renal dysfunction (e.g. chronic renal failure); (f) atherosclerosis (arteriosclerosis); (g) cardioprotection; (h) allograft survival; (i) cerebral ischemia; (j) coronary vasospasm; and (k) vascular inflammation.

Other applicable diseases and conditions include muscle (e.g. smooth muscle) dysfunction, for example selected from: (a) asthma; (b) penile erectile dysfunction; (c) female sexual dysfunction; (d) over-active bladder I syndrome; and (e) abnormal smooth muscle (e.g. associated with hypertension).

Other applicable diseases and conditions include inflammation, wherein for example the inflammation comprises or is manifest by: (a) rheumatoid arthritis; (b) irritable bowel syndrome; (c) inflammatory bowel disease; (d) vascular inflammation, and (e) a neuroinflammatory disease or condition.

In embodiments relating to neuroinflammatory diseases or conditions, these may be selected from: (a) stroke; (b) multiple sclerosis; (c) Alzheimer's disease; (d) Parkinson's disease; (e) amyotrophic lateral sclerosis; and (f) inflammatory pain.

Other applicable diseases and conditions include CNS diseases or conditions, including those selected from: (a) spinal cord injury or trauma; (b) brain injury or trauma; (c) acute neuronal injury (e.g. stroke or traumatic brain injury); (d) Parkinson's disease; (e) Alzheimer's disease; (f) neurodegenerative conditions or diseases; (g) stroke (e.g. associated with hypertension); (h) cerebral vasospasm; (i) inhibition of neurite growth and sprouting; (j) inhibited neurite regeneration; (k) compromised post-trauma functional recovery; (l) demyelinating diseases or disorders; (m) inflammatory CNS diseases or disorders; (n) neuropathic pain; and (o) neurodegeneration.

Other applicable CNS diseases or conditions include those selected from: Downs syndrome and β-amyloid angiopathy, such as but not limited to cerebral amyloid angiopathy, hereditary cerebral hemorrhage, disorders associated with cognitive impairment, such as but not limited to MCI ("mild cognitive impairment"), Alzheimer Disease, memory loss, attention deficit symptoms associated with Alzheimer disease, neurodegeneration associated with diseases such as Alzheimer Disease or dementia including dementia of mixed vascular and degenerative origin, pre-senile dementia, senile dementia and dementia associated with Parkinson's Disease, progressive supranuclear palsy or cortical basal degeneration, Parkinson's Disease, Frontotemporal dementia Parkinson's Type, Parkinson dementia complex of Guam, HIV dementia, diseases with associated neurofibrillar tangle pathologies, dementia pugilistica, amyotrophic lateral sclerosis, corticobasal degeneration, Down syndrome, Huntington's Disease, postencephelatic parkinsonism, progressive supranuclear palsy, Pick's Disease, Niemann-Pick's Disease, stroke, head trauma and other chronic neurodegenerative diseases, Bipolar Disease, affective disorders, depression, anxiety, schizophrenia, cognitive disorders, hair loss, contraceptive medication, predemented states, Age-Associated Memory Impairment, Age-Related Cognitive Decline, Cognitive Impairement No Dementia, mild cognitive decline, mild neurocognitive decline, Late-Life Forgetfulness, memory impairment and cognitive impairment, vascular dementia, dementia with Lewy bodies, Frontotemporal dementia and androgenetic alopecia.

Yet other applicable diseases and conditions include: (a) insulin resistance; (b) graft protection (e.g. cardiovascular or inflammatory graft protection); (c) diabetes; (d) asthma; (e) pulmonary vasoconstriction; (f) glaucoma; and (g) fibroses (e.g. liver fibrosis and kidney fibrosis).

Other applicable diseases and conditions include infectious diseases or conditions, including metazoan, protozoan, fungal, prion, viral or bacterial infestations, diseases or infections.

In such embodiments, the infectious disease or condition may comprise pathogen-mediated cytoskeletal rearrangement.

Proliferative Disorders (Including Cancers):

The invention also finds application as a means of preventing the growth of or inducing apoptosis of neoplasias. It is therefore anticipated that the invention will prove useful in treating or preventing proliferative disorders such as cancers.

Examples of such abnormalities include but are not limited to overexpression of one or more of the Rho signalling pathway members, or mutations in said members which lead to an increase in the basal activity of ROCK kinase(s) or the Rho signalling pathway (which may for example be associated with upregulation or overexpression or mutational activation of a growth factor receptor such as a growth factor selected from the epidermal growth factor receptor (EGFR), fibroblast growth factor receptor (FGFR), platelet derived growth factor receptor (PDGFR), insulin-like growth factor 1 receptor (IGF-1R) and vascular endothelial growth factor receptor (VEGFR) families).

It is also envisaged that the invention will be useful in treating other conditions which result from disorders in proliferation or survival such as viral infections, and neurodegenerative diseases for example.

The invention therefore finds broad application in the treatment of diseases in which there is a disorder of proliferation, apoptosis or differentiation.

Examples of cancers which may be inhibited include, but are not limited to, a carcinoma, for example a carcinoma of the bladder, breast, colon (e.g. colorectal carcinomas such as colon adenocarcinoma and colon adenoma), kidney, epidermal, liver, lung, for example adenocarcinoma, small cell lung cancer and non-small cell lung carcinomas, oesophagus, gall bladder, ovary, pancreas e.g. exocrine pancreatic carcinoma, stomach, cervix, endometrium, thyroid, prostate, or skin, for example squamous cell carcinoma; a hematopoietic tumour of lymphoid lineage, for example leukaemia, acute lymphocytic leukaemia, B-cell lymphoma, T-cell lymphoma, Hodgkin's lymphoma, non-Hodgkin's lymphoma, hairy cell lymphoma, or Burkett's lymphoma; a hematopoietic tumour of myeloid lineage, for example acute and chronic myelogenous leukaemias, myelodysplastic syndrome, or promyelocytic leukaemia; thyroid follicular cancer; a tumour of mesenchymal origin, for example fibrosarcoma or rhabdomyosarcoma; a tumour of the central or peripheral nervous system, for example astrocytoma, neuroblastoma, glioma or schwannoma; melanoma; seminoma; teratocarcinoma; osteosarcoma; xenoderoma pigmentosum; keratoctanthoma; thyroid follicular cancer; or Kaposi's sarcoma.

A further example of a hematopoietic tumour of lymphoid lineage is multiple myeloma.

Particular subsets of cancers include breast cancer, ovarian cancer, colon cancer, prostate cancer, oesophageal cancer, squamous cancer and non-small cell lung carcinomas. A further subset of cancers includes breast cancer, ovarian cancer, prostate cancer, endometrial cancer and glioma.

Another example of a disorder of proliferation is myeloproliferative syndrome.

Immune Disorders:

Immune disorders for which the invention may be beneficial include but are not limited to autoimmune conditions and chronic inflammatory diseases, for example systemic lupus erythematosus, autoimmune mediated glomerulonephritis, rheumatoid arthritis, psoriasis, inflammatory bowel disease, and autoimmune diabetes mellitus, Eczema hypersensitivity reactions, asthma, COPD, rhinitis, and upper respiratory tract disease.

Other Therapeutic Uses:

ROCK-mediated physiological processes play a role in apoptosis, proliferation, differentiation and therefore the invention could also be useful in the treatment of the following diseases other than cancer and those associated with immune dysfunction; viral infections, for example herpes virus, pox virus, Epstein-Barr virus, Sindbis virus, adenovirus, HIV, HPV, HCV and HCMV; prevention of AIDS development in HIV-infected individuals; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, degenerative diseases of the musculoskeletal system, for example, osteoporosis and arthritis, aspirin-sensitive rhinosinusitis, cystic fibrosis, multiple sclerosis, kidney diseases.

The invention may also be useful in diseases resulting from insulin resistance and insensitivity, and the disruption of glucose, energy and fat storage such as metabolic disease and obesity.

The invention contemplates ROCK-mediated intervention, treatment or prophylaxis of any kind. Thus, the invention finds application in relation to treatment or prophylaxis comprising: (a) the modulation (e.g. inhibition) of ROCK kinase; or (b) intervention at the level of the activity of ROCK kinase; or (c) intervention at the level of the Rho signalling pathway (e.g. at the level of RhoA and. or RhoC).

Other applicable methods include interventions which effect: (a) muscle (e.g. smooth muscle) relaxation; (b) vascular muscle relaxation (e.g. to increase vascular blood flow); (c) nerve cell modulation; (d) reduction of cell proliferation; (e) reduction of cell migration; (f) suppression of cytoskeletal rearrangement upon pathogen invasion or infection; (g) acceleration of tissue regeneration; and (h) enhancement of post-traumatic functional recovery.

In such embodiments, the nerve cell modulation may comprise: (a) neuronal regeneration; (b) new axonal growth induction; (c) axonal rewiring across lesions within the CNS; (d) neurite outgrowth; (e) neurite differentiation; (f) axon pathfinding; (g) dendritic spine formation; (h) dendritic spine maintenance; (i) modulation of neurite growth cone collapse; and (j) modulation of neurite outgrowth inhibition.

Other applicable treatments include transplantation therapy (e.g. comprising graft protection).

Yet other applicable methods comprise a method of diagnosis and treatment of a disease state or condition, which method comprises: (i) screening a patient to determine whether a disease or condition from which the patient is or may be suffering is one which would be susceptible to treatment with a compound having activity against ROCK kinase; and (ii) where it is indicated that the disease or condition from which the patient is thus susceptible, thereafter administering to the patient a compound according to the invention.

The subject or patient population may be selected from: (a) those in which ROCK kinase is dysfunctional (for example, hyperactive); and (b) those which have been subject to diagnostic tests for ROCK dysfunction (e.g. for ROCK hyperactivity); (c) those in which the Rho signalling pathway is dysfunctional; and (d) those which have been subject to diagnostic tests for Rho signalling pathway dysfunction.

Uses Associated with or Arising from p70S6K Kinase Inhibitory Activity

The compounds of formula (I) modulate (e.g. inhibit) the activity of protein kinase p70S6K. The compounds therefore find application in: (a) the treatment or prophylaxis of a disease or condition in which the modulation (e.g. inhibition) of protein kinase p70S6K is indicated; and/or (b) the treatment of a subject or patient population in which the modulation (e.g. inhibition) of protein kinase p70S6K is indicated.

The invention therefore finds application in relation to conditions selected from: (a) cancer (e.g. p70S6K-mediated cancer); (b) tumour metastases; (c) immune dysfunction; (d)

tissue damage (e.g. arising from inflammation); (e) chromosome 17q23 amplification (or conditions arising therefrom or associated therewith); (f) Peutz-Jeghers syndrome (or conditions arising therefrom or associated therewith); (g) LKB 1 mutation(s) (or conditions arising therefrom or associated therewith); (h) BRCA1 mutation(s) (or conditions arising therefrom or associated therewith); (i) BRCA2 mutation(s) (or conditions arising therefrom or associated therewith); (j) dysfunctional apoptotic programmes; (k) growth factor receptor signal transduction, overexpression and activation in tumour tissue; (l) a metabolic disease or disorder; (m) those associated with abnormal cell proliferation and/or metabolism; and (n) neuronal disorders.

In such embodiments, the disease or condition arising from or associated with chromosome 17q23 amplification may be selected from: (a) primary breast tumours; (b) tumours (e.g. breast tumours) containing BRCA2 mutations; (c) tumours (e.g. breast tumours) containing BRCA1 mutations; (d) pancreatic tumours; (e) bladder tumours; and (f) neuroblastomas.

The disease or condition arising from or associated with LKB1 mutation(s) may be lung adenocarcinoma containing LKB1 mutation(s) (e.g. inactivating LKB1 mutation(s)).

The disease or condition arising from or associated with BRCA1/2 mutation(s) may be breast cancer.

The metabolic disease or disorder may be selected from: (a) obesity (for example age-induced obesity or diet-induced obesity); (b) diabetes; (c) metabolic syndrome; (d) insulin resistance; (e) hyperglycemia; (f) hyperaminoacidemia; and (g) hyperlipidmia.

Proliferative Disorders (Including Cancers):

The invention also finds application as a means of preventing the growth of or inducing apoptosis of neoplasias. It is therefore anticipated that the invention will prove useful in treating or preventing proliferative disorders such as cancers. Examples of such abnormalities include but are not limited to overexpression of p70S6K (or the other syndromes described herein).

It is also envisaged that the invention will be useful in treating other conditions which result from disorders in proliferation or survival such as viral infections, and neurodegenerative diseases for example.

The invention therefore finds broad application in the treatment of diseases in which there is a disorder of proliferation, apoptosis or differentiation.

Examples of cancers which may be inhibited include, but are not limited to, a carcinoma, for example a carcinoma of the bladder, breast, colon (e.g. colorectal carcinomas such as colon adenocarcinoma and colon adenoma), kidney, epidermal, liver, lung, for example adenocarcinoma, small cell lung cancer and non-small cell lung carcinomas, oesophagus, gall bladder, ovary, pancreas e.g. exocrine pancreatic carcinoma, stomach, cervix, endometrium, thyroid, prostate, or skin, for example squamous cell carcinoma; a hematopoietic tumour of lymphoid lineage, for example leukaemia, acute lymphocytic leukaemia, B-cell lymphoma, T-cell lymphoma, Hodgkin's lymphoma, non-Hodgkin's lymphoma, hairy cell lymphoma, or Burkitt's lymphoma; a hematopoietic tumour of myeloid lineage, for example acute and chronic myelogenous leukaemias, myelodysplastic syndrome, or promyelocytic leukaemia; thyroid follicular cancer; a tumour of mesenchymal origin, for example fibrosarcoma or rhabdomyo sarcoma; a tumour of the central or peripheral nervous system, for example astrocytoma, neuroblastoma, glioma or schwannoma; melanoma; seminoma; teratocarcinoma; osteosarcoma; xenoderoma pigmentosum; keratoctanthoma; thyroid follicular cancer; or Kaposi's sarcoma.

A further example of a hematopoietic tumour of lymphoid lineage is multiple myeloma.

Particular subsets of cancers include breast cancer, ovarian cancer, colon cancer, prostate cancer, oesophageal cancer, squamous cancer and non-small cell lung carcinomas. A further subset of cancers includes breast cancer, ovarian cancer, prostate cancer, endometrial cancer and glioma.

Another example of a disorder of proliferation is myeloproliferative syndrome.

Immune Disorders:

Immune disorders for which the invention may be beneficial include but are not limited to autoimmune conditions and chronic inflammatory diseases, for example systemic lupus erythematosus, autoimmune mediated glomerulonephritis, rheumatoid arthritis, psoriasis, inflammatory bowel disease, and autoimmune diabetes mellitus, Eczema hypersensitivity reactions, asthma, COPD, rhinitis, and upper respiratory tract disease.

Other Therapeutic Uses:

p70S6K-mediated physiological processes play a role in apoptosis, proliferation, differentiation and therefore the invention could also be useful in the treatment of the following diseases other than cancer and those associated with immune dysfunction; viral infections, for example herpes virus, pox virus, Epstein-Barr virus, Sindbis virus, adenovirus, HIV, HPV, HCV and HCMV; prevention of AIDS development in HIV-infected individuals; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, degenerative diseases of the musculoskeletal system, for example, osteoporosis and arthritis, aspirin-sensitive rhinosinusitis, cystic fibrosis, multiple sclerosis, kidney diseases.

The invention may also be useful in diseases resulting from insulin resistance and insensitivity, and the disruption of glucose, energy and fat storage such as metabolic disease and obesity.

The invention contemplates protein kinase p70S6K-mediated intervention, treatment or prophylaxis of any kind. Thus, the invention finds application in relation to treatment or prophylaxis comprising: (a) the modulation (e.g. inhibition) of protein kinase p70S6K; (b) intervention at the level of the activity of protein kinase p70S6K; (b) inhibition of progression from G1 to S phase in the cell cycle in vivo; (c) inhibition of cell cycle proliferation at the G1 to S phase of the cell cycle; (d) use of a compound of formula (I) as a rapamycin surrogate; (e) use of a compound of formula (I) as a wortmannin surrogate; (f) the re-establishment of appropriate apoptotic programmes; (g) the inhibition of growth factor receptor signal transduction, overexpression and activation in tumour tissue; (h) modulation of neuronal cell differentiation; (i) modulation of cell motility; (j) modulation of cellular response(s); and (k) enhancing insulin sensitivity.

The treatment or prophylaxis may also comprise a method of diagnosis and treatment of a disease state or condition, which method comprises: (i) screening a patient to determine whether a disease or condition from which the patient is or may be suffering is one which would be susceptible to treatment with a compound having activity against protein kinase p70S6K; and (ii) where it is indicated that the disease or condition from which the patient is thus susceptible, thereafter administering to the patient a compound of formula (I) as herein defined.

The subject or patient population may be selected from: (a) those in which protein kinase p70S6K is dysfunctional (for example, hyperactive); (b) those which have been subject to diagnostic tests for p70S6K is dysfunction (e.g. for p70S6K hyperactivity); (c) those in which chromosome 17q23 is amplified; and (d) those which have been subject to diagnostic tests for amplification of chromosome 17q23; (e) those in which BRCA1 mutation(s) are present; (f) those which have been subject to diagnostic tests for BRCA1 mutation(s); (g) those in which BRCA2 mutation(s) are present; (h) those which have been subject to diagnostic tests for BRCA2 mutation(s); (i) those in which LKB1 mutation(s) are present; (j) those which have been subject to diagnostic tests for LKB1 mutation(s); and (k) those which have been screened as defined herein.

Advantages of the Compositions of the Invention

Potentially the compositions of the invention have physiochemical properties suitable for oral exposure.

The composition as defined herein should exhibit improved oral bioavailability relative to prior art compounds. Oral bioavailability can be defined as the ratio (F) of the plasma exposure of a compound when dosed by the oral route to the plasma exposure of the compound when dosed by the intravenous (i.v.) route, expressed as a percentage.

Compositions having an oral bioavailability (F value) of greater than 30%, more preferably greater than 40%, are particularly advantageous in that they may be administered orally rather than, or as well as, by parenteral administration.

Furthermore, the compound of formula (I) is both more potent and more selective in its activities against different kinases, and demonstrates enhanced selectivity for and potency against PKB in particular.

The compound of formula (I) is significantly more potent than its R-enantiomer at inhibiting PKB in vitro and in cells. The $IC_{50}$ for the compound of formula (I) against the isolated PKB enzyme in an in vitro radiometric assay is 0.01 µM compared to 0.96 µM for the R-enantiomer. This approximate 100-fold difference in potency is also observed in a cell-based mechanistic assay which measures phosphorylation of GSK3β, a direct downstream substrate of PKB. The compound of formula (I) displays an $IC_{50}$ of 1.1 µM, compared to a value for the R-enantiomer of >50 µM.

An additional difference between the 2 enantiomers is in their potency against the closely related kinase PKA, where the compound of formula (I) inhibits the isolated enzyme at 44% at 0.03 µM compared to the R-enantiomer which inhibits PKA at 0.25 µM.

The compound of formula (I) is advantageous over prior art compounds in that it has different susceptibilities to P450 enzymes and in that it exhibits improvements with regard to drug metabolism and pharmacokinetic properties. For example, the compound of formula (I) has $IC_{50}$ values of greater than 10 µM against each of the cytochrome P450 enzymes 1A2, 2C9, 2C19, 3A4 and 2D6.

Furthermore, the compound of formula (I) should exhibit reduced dosage requirements.

The compound of formula (I) is potentially less toxic than prior art compounds.

hERG

In the late 1990s a number of drugs, approved by the US FDA, had to be withdrawn from sale in the US when it was discovered they were implicated in deaths caused by heart malfunction. It was subsequently found that a side effect of these drugs was the development of arrhythmias caused by the blocking of hERG channels in heart cells. The hERG channel is one of a family of potassium ion channels the first member of which was identified in the late 1980s in a mutant *Drosophila melanogaster* fruitfly (see Jan, L. Y. and Jan, Y. N. (1990). A Superfamily of Ion Channels. *Nature,* 345(6277): 672). The biophysical properties of the hERG potassium ion channel are described in Sanguinetti, M. C., Jiang, C., Curran, M. E., and Keating, M. T. (1995). A Mechanistic Link Between an Inherited and an Acquired Cardiac Arrhythmia: HERG encodes the Ikr potassium channel. *Cell,* 81:299-307, and Trudeau, M. C., Warmke, J. W., Ganetzky, B., and Robertson, G. A. (1995). HERG, a Human Inward Rectifier in the Voltage-Gated Potassium Channel Family. *Science,* 269:92-95.

The elimination of hERG blocking activity remains an important consideration in the development of any new drug.

The compounds of formula (I) has negligible hERG ion channel blocking activity.

Methods of Treatment

The composition as defined herein will be useful in the prophylaxis or treatment of a range of disease states or conditions mediated by protein kinase A and/or protein kinase B and/or a ROCK kinase and/or p70S6K kinase. Examples of such disease states and conditions are set out above.

The compositions are generally administered to a subject in need of such administration, for example a human or animal patient, preferably a human.

The composition will typically be administered in amounts that are therapeutically or prophylactically useful and which generally are non-toxic. However, in certain situations (for example in the case of life threatening diseases), the benefits of administering a composition as defined herein may outweigh the disadvantages of any toxic effects or side effects, in which case it may be considered desirable to administer compounds in amounts that are associated with a degree of toxicity.

The compositions may be administered over a prolonged term to maintain beneficial therapeutic effects or may be administered for a short period only. Alternatively they may be administered in a pulsatile or continuous manner.

A typical daily dose of the compound of formula (I) can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The composition as defined herein can be administered on a daily basis or on a repeat basis every 2, or 3, or 4, or 5, or 6, or 7, or 10 or 14, or 21, or 28 days for example.

The compound of formula (I) may be administered orally in a range of doses, for example 1 to 1500 mg, 2 to 800 mg, or 5 to 500 mg, e.g. 2 to 200 mg or 10 to 1000 mg, particular examples of doses including 10, 20, 50 and 80 mg. The compound may be administered once or more than once each day. The compound can be administered continuously (i.e. taken every day without a break for the duration of the treatment regimen). Alternatively, the compound can be administered intermittently, i.e. taken continuously for a given period such as a week, then discontinued for a period such as a week and then taken continuously for another period such as a week and so on throughout the duration of the treatment regimen. Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles.

In one particular dosing schedule, a patient will be given an infusion of a composition as defined herein for periods of one hour daily for up to ten days in particular up to five days for one week, and the treatment repeated at a desired interval such as two to four weeks, in particular every three weeks.

More particularly, a patient may be given an infusion of a composition as defined herein for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, an in particular a continuous infusion of 24 hours to 72 hours.

Ultimately, however, the quantity of compound administered and the type of composition used will be commensurate with the nature of the disease or physiological condition being treated and will be at the discretion of the physician.

The compound of formula (I) can be administered as the sole therapeutic agent or they can be administered in combination therapy with one or more other compounds for treatment of a particular disease state, for example a neoplastic disease such as a cancer as hereinbefore defined. Examples of other therapeutic agents or treatments that may be administered together (whether concurrently or at different time intervals) with the compounds of the formula (I) include but are not limited to:

Topoisomerase I inhibitors
Antimetabolites
Tubulin targeting agents
DNA binder and topoisomerase II inhibitors
Alkylating Agents
Monoclonal Antibodies.
Anti-Hormones
Signal Transduction Inhibitors
Proteasome Inhibitors
DNA methyl transferases
Cytokines and retinoids
Chromatin targeted therapies
Radiotherapy, and,
Other therapeutic or prophylactic agents; for example agents that reduce or alleviate some of the side effects associated with chemotherapy. Particular examples of such agents include anti-emetic agents and agents that prevent or decrease the duration of chemotherapy-associated neutropenia and prevent complications that arise from reduced levels of red blood cells or white blood cells, for example erythropoietin (EPO), granulocyte macrophage-colony stimulating factor (GM-CSF), and granulocyte-colony stimulating factor (G-CSF). Also included are agents that inhibit bone resorption such as bisphosphonate agents e.g. zoledronate, pamidronate and ibandronate, agents that suppress inflammatory responses (such as dexamethasone, prednisone, and predniso lone) and agents used to reduce blood levels of growth hormone and IGF-I in acromegaly patients such as synthetic forms of the brain hormone somatostatin, which includes octreotide acetate which is a long-acting octapeptide with pharmacologic properties mimicking those of the natural hormone somatostatin. Further included are agents such as leucovorin, which is used as an antidote to drugs that decrease levels of folic acid, or folinic acid it self and agents such as megestrol acetate which can be used for the treatment of side-effects including oedema and thromboembolic episodes.

Each of the compounds present in the combinations of the invention may be given in individually varying dose schedules and via different routes.

Where the compound of the formula (I) is administered in combination therapy with one, two, three, four or more other therapeutic agents (preferably one or two, more preferably one), the compounds can be administered simultaneously or sequentially. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s).

The compound of formula (I) may also be administered in conjunction with non-chemotherapeutic treatments such as radiotherapy, photodynamic therapy, gene therapy; surgery and controlled diets.

For use in combination therapy with another chemotherapeutic agent, the composition as defined herein and one, two, three, four or more other therapeutic agents can be, for example, formulated together in a dosage form containing two, three, four or more therapeutic agents. In an alternative, the individual therapeutic agents may be formulated separately and presented together in the form of a kit, optionally with instructions for their use.

A person skilled in the art would know through his or her common general knowledge the dosing regimes and combination therapies to use.

Methods of Diagnosis

Prior to administration of a composition as defined herein, a patient may be screened to determine whether a disease or condition from which the patient is or may be suffering is one which would be susceptible to treatment with a compound having activity against a particular target kinase (e.g. protein kinase A and/or protein kinase B and/or ROCK kinase and/or P70S6K kinase).

For example, a biological sample taken from a patient may be analysed to determine whether a condition or disease, such as cancer, that the patient is or may be suffering from is one which is characterised by a genetic abnormality or abnormal protein expression which leads to up-regulation of PKA and/or PKB or to sensitisation of a pathway to normal PKA and/or PKB activity, or to upregulation of a signal transduction component upstream of PKA and/or PKB such as, in the case of PKB, P13K, GF receptor and PDK 1 & 2.

Alternatively, a biological sample taken from a patient may be analysed for loss of a negative regulator or suppressor of the PKB pathway such as PTEN. In the present context, the term "loss" embraces the deletion of a gene encoding the regulator or suppressor, the truncation of the gene (for example by mutation), the truncation of the transcribed product of the gene, or the inactivation of the transcribed product (e.g. by point mutation) or sequestration by another gene product.

Alternatively, or additionally, the patient may be screened for dysfunction in ROCK activity (e.g. elevated or up-regulated ROCK expression, mutations in ROCK genes or ROCK gene regulatory elements) or Rho signalling dysfunction (as described herein).

The term up-regulation includes elevated expression or over-expression, including gene amplification (i.e. multiple gene copies) and increased expression by a transcriptional effect, and hyperactivity and activation, including activation by mutations. Thus, the patient may be subjected to a diagnostic test to detect a marker characteristic of up-regulation of a kinase (e.g. PKA and/or PKB and/or ROCK kinase and/or P70S6K kinase). The term diagnosis includes screening. By marker we include genetic markers including, for example, the measurement of DNA composition to identify mutations of the kinase (e.g. PKA and/or PKB and/or ROCK kinase and/or P70S6K kinase). The term marker also includes markers which are characteristic of up regulation of the kinase (e.g. PKA and/or PKB and/or ROCK kinase and/or P70S6K kinase) and/or other factors which lead to an upregulation of the relevant pathways, including enzyme activity, enzyme levels, enzyme state (e.g. phosphorylated or not) and mRNA levels of the aforementioned proteins.

The above diagnostic tests and screens are typically conducted on a biological sample selected from tumour biopsy samples, blood samples (isolation and enrichment of shed tumour cells), stool biopsies, sputum, chromosome analysis, pleural fluid, peritoneal fluid, bone marrow or urine.

Identification of an individual carrying a mutation in PKA and/or PKB or a rearrangement of TCL-1 or loss of PTEN expression may mean that the patient would be particularly suitable for treatment with a PKA and/or PKB inhibitor. Tumours may preferentially be screened for presence of a PKA and/or PKB variant prior to treatment. The screening process will typically involve direct sequencing, oligonucleotide microarray analysis, or a mutant specific antibody.

Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridisation.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. Current Protocols in Molecular Biology, 2004, John Wiley & Sons Inc., or Innis, M. A. et-al., eds. PCR Protocols: a guide to methods and applications, 1990, Academic Press, San Diego. Reactions and manipulations involving nucleic acid techniques are also described in Sambrook et al., 2001, $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference.

An example of an in-situ hybridisation technique for assessing mRNA expression would be fluorescence in-situ hybridisation (FISH) (see Angerer, 1987 Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labeled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions.

Standard methods for carrying out FISH are described in Ausubel, F. M. et al., eds. Current Protocols in Molecular Biology, 2004, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of the kinase (e.g. PKB and/or PKA and/or ROCK kinase and/or P70S6K kinase), or detection of kinase variants could be applicable in the present case.

Therefore all of these techniques could also be used to identify tumours particularly suitable for treatment with PKA and/or PKB and/or ROCK kinase and/or P70S6K kinase inhibitors.

For example, as stated above, PKB beta has been found to be upregulated in 10-40% of ovarian and pancreatic cancers (Bellacosa et al 1995, Int. J. Cancer 64, 280-285; Cheng et al 1996, PNAS 93, 3636-3641; Yuan et al 2000, Oncogene 19, 2324-2330). Therefore it is envisaged that PKB inhibitors, and in particular inhibitors of PKB beta, may be used to treat ovarian and pancreatic cancers.

PKB alpha is amplified in human gastric, prostate and breast cancer (Staal 1987, PNAS 84, 5034-5037; Sun et al 2001, Am. J. Pathol. 159, 431-437). Therefore it is envisaged that PKB inhibitors, and in particular inhibitors of PKB alpha, may be used to treat human gastric, prostate and breast cancer.

Increased PKB gamma activity has been observed in steroid independent breast and prostate cell lines (Nakatani et al 1999, J. Biol. Chem. 274, 21528-21532). Therefore it is envisaged that PKB inhibitors, and in particular inhibitors of PKB gamma, may be used to treat steroid independent breast and prostate cancers.

Detection of ROCK may be carried out at either the mRNA or protein level. Specific examples of methods where levels of Rho and ROCK have been determined in clinical samples include:

American Journal of Pathology. 2002; 160:579-584. This paper describes immunohistochemistry performed on formalin-fixed tissues to characterize RhoC expression in human breast tissues.

Clinical Cancer Research Vol. 9, 2632-2641, July 2003. This paper describes the use of Western blotting to quantitate Rho and ROCK protein expression in paired tumour and nontumour surgical samples from 107 consecutive Japanese patients with bladder cancer.

Pancreas. 24(3):251-257, April 2002. This paper describes the expression of ROCK-1 in human pancreatic tissues by immunoblotting and immunohistochemistry.

World J Gastroenterol 2003 September; 9(9):1950-1953. This paper describes the examination of mRNA expression levels of RhoC gene by reverse transcription-polymerase chain reaction (RT-PCR) in hepatocellular carcinoma (HCC).

The relevant methodological disclosure relating to the quantitation of the levels of Rho and/or ROCK activity or expression contained in the above-mentioned publications are hereby incorporated herein by reference.

Detection of p70S6K may be carried out at either the mRNA or protein level. Exemplary methods are described for example in J Naltl Cancer Inst (2000): 92, pp. 1252-9 (which describes detecting the activation of Ribosomal Protein S6 Kinase by complementary DNA and tissue microarray analysis uses comparative genomic hybridization (CGH) and cDNA and tissue microarray analyses to identify amplified and overexpressed genes).

The detection of overexpressed p70S6K is described in Int J Oncol (2004): 24 (4), pp. 893-900. This paper describes the pharmacolgenomic profiling of the PI3K/PTEN-Akt-mTOR pathway in common human tumours using immunohistoochemistry to compare high p70S6K, AKT expression to tumour sensitivity.

EXPERIMENTAL

The invention will now be illustrated, but not limited, by reference to the specific embodiments described in the following procedures and examples.

The starting materials for each of the procedures described below are commercially available unless otherwise specified.

Proton magnetic resonance ($^1$H NMR) spectra were recorded on a Bruker AV400 instrument operating at 400.13 MHz, in Me-d$_3$-OD at 27° C., unless otherwise stated and are reported as follows: chemical shift δ/ppm (number of protons, multiplicity where s=singlet, d=doublet, t=triplet, q=quartet, m=multiplet, br=broad). The residual protic solvent MeOH ($δ_H$=3.31 ppm) was used as the internal reference.

In the examples, the compounds prepared were characterised by liquid chromatography and mass spectroscopy using the systems and operating conditions set out below. Where chlorine is present, the mass quoted for the compound is for $^{35}$Cl. The operating conditions used are described below.

Platform System
HPLC System: Waters 2795
Mass Spec Detector: Micromass Platform LC
PDA Detector: Waters 2996 PDA
Acidic Analytical Conditions 2:
Eluent A: H$_2$O (0.1% Formic Acid)
Eluent B: CH$_3$CN (0.1% Formic Acid)
Gradient: 5-95% eluent B over 3.5 minutes
Flow: 0.8 ml/min
Column: Phenomenex Synergi 4μ Max-RP 80A, 50×2.0 mm
Basic Analytical Conditions 5:
Eluent A: H$_2$O (10 mM NH$_4$HCO$_3$ buffer adjusted to pH=9.2 with NH$_4$OH)
Eluent B: CH$_3$CN
Gradient: 05-95% eluent B over 3.5 minutes
Flow: 0.8 ml/min
Column: Phenomenex Gemini 5'1 2.0×50 mm
MS Conditions:
Capillary voltage: 3.5 kV or 3.6 kV
Cone voltage: 30 V
Source Temperature: 120° C.
Scan Range: 165-700 amu
Ionisation Mode: ElectroSpray Negative, Positive or Positive & Negative In the examples below, the following key is used to identify the LCMS conditions used:
PS-A2 Platform System—acidic analytical conditions 2
PS-B5 Platform System—basic analytical conditions 5

Example 1

Preparation of (S)-2-amino-1-(4-chloro-phenyl)-1-[4-(1H-pyrazol-4-yl)-phenyl]-ethanol 1A. 2-(4-Chloro-phenyl)-2-(4-iodo-phenyl)-oxirane

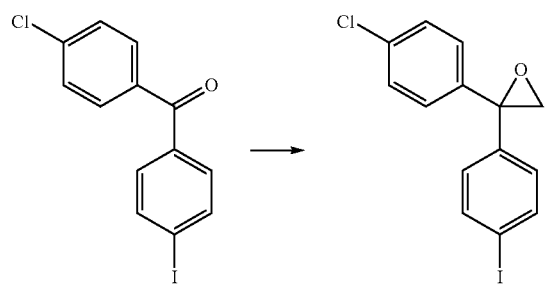 [SMILES: O=C(c1ccc(Cl)cc1)c1ccc(I)cc1 ; Clc1ccc(C2(c3ccc(I)cc3)CO2)cc1]

Sodium hydride (60% dispersion in oil, 128 mg, 3.2 mmol) was placed under N$_2$ then DMSO (5 mL) was added. Trimethylsulfonium iodide (0.66 g, 3.2 mmol) was added as a solid after 15 minutes, followed after a further 30 minutes by (4-chloro-phenyl)-(4-iodo-phenyl)-methanone (1 g, 2.9 mmol). The mixture was stirred at room temperature for 24 hours then diluted with ethyl acetate and washed with 1:2 water/brine, water and brine (×2). The organic phase was dried (MgSO$_4$), filtered and concentrated to give the title compound (1.01 g, 97%), which was used without further purification. LCMS (PS-A2) R$_t$ 4.07 min [M−H]$^-$ 355.

1B. 2-Amino-1-(4-chloro-phenyl)-1-[4-iodo-phenyl]-ethanol (Epoxide ring opening reaction)

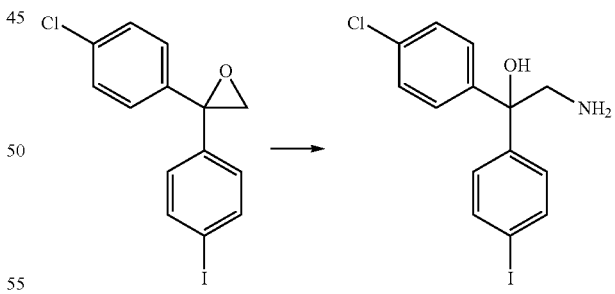

2-(4-Chloro-phenyl)-2-(4-iodo-phenyl)-oxirane (500 mg, 1.40 mmol) was dissolved in 2M NH$_3$ in methanol (5 ml, 10.0 mmol) and the solution was heated in a microwave at 130° C. for 60 minutes. Upon cooling, the solvent was removed in vacuo to furnish the desired product. Three identical reactions were carried out and afforded 1.55 g (98%) of the product 2-amino-1-(4-chloro-phenyl)-1-[4-iodo-phenyl]-ethanol. The crude product was pure and was used in the next step without purification.

1C. [2-(4-Chloro-phenyl)-2-hydroxy-2-(4-iodo-phenyl)-ethyl]-carbamic acid tert-butyl ester (BOC protection)

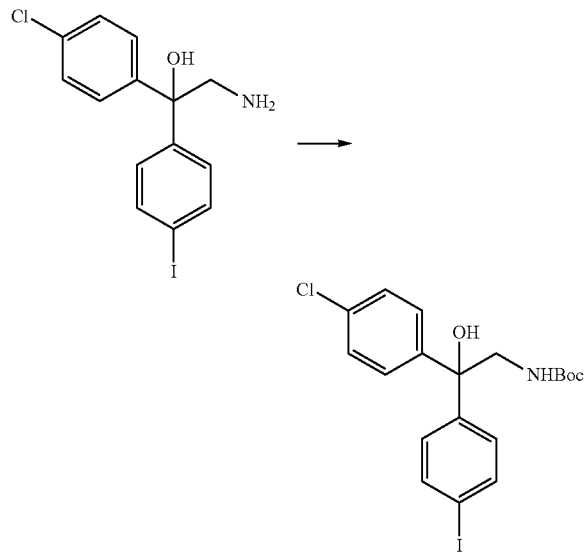

The amino alcohol product of step 1B (9.55 g, 25.56 mmol) was suspended in 1,4-dioxane (220 ml) and 2M NaOH added (16.6 ml, 33.24 mmol). The mixture was stirred vigorously until homogenous. Di-tert-butyl dicarbonate (6.14 g, 28.11 mmol) was added and the reaction mixture was stirred at 45 C for 20 hours. Upon cooling, the reaction mixture was concentrated and partitioned between EtOAc (150 ml) and water (150 ml). The organic layer was separated and washed with Brine (150 ml), dried (MgSO$_4$) and concentrated to yield a yellow oil (14.08 g). The crude product was purified by flash chromatography using a Biotage SP4 (65i column) eluting with ethyl acetate-petrol (5%-40% EtOAc gradient) to afford the title compound as a white solid (10.0 g, 83%). R$_t$ 3.73 min [M+H] 473.96

1D. [2-(4-Chloro-phenyl)-2-hydroxy-2-[4-(1H-pyrazol-4-yl)-phenyl]-ethyl]-carbamic acid tert-butyl ester (Suzuki coupling reaction)

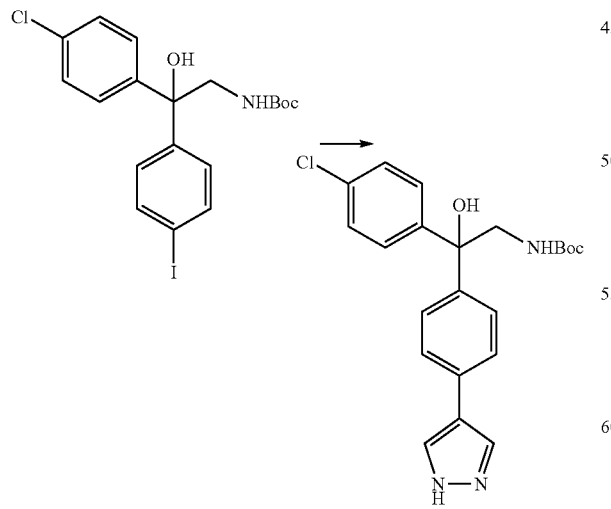

[2-(4-Chloro-phenyl)-2-hydroxy-2-(4-iodo-phenyl)-ethyl]-carbamic acid tert-butyl ester (5 g, 10.6 mmol) was combined with 4-(4,4,5,5-tetramethyl-[1,3,2]dioxaborolan-2-yl)-1H-pyrazole (4.1 g, 21.11 mmol) and potassium phosphate (tribasic, 7.88 g, 37.10 mmol) in a round-bottomed flask. The solids were then dissolved in a solvent mixture of 1:1:1:1 ethanol, methanol, toluene and water (33 mL of each solvent). The solution was degassed with nitrogen and tetrakistriphenylphosphine palladium (0) (0.612 g, 0.53 mmol) was added. The mixture was degassed with nitrogen and then heated at 85° C. under nitrogen for 2 hours. The reaction mixture was then allowed to cool to room temperature. Additional batches of reagents were then added: potassium phosphate (7.88 g, 37.10 mmol) and pyrazole boronate (4.1 g, 21.11 mmol). The reaction mixture was degassed with nitrogen and a further batch of tetrakistriphenylphosphine palladium (0) (0.101 g, 0.087 mmol) was added. The reaction mixture was degassed and then heated at 85° C. under nitrogen for 17 hours. Additional batches of reagents were added again (refer to quantities above) and heating was continued at 85° C. under nitrogen for a further 6.5 hours. The reaction mixture was then allowed to cool to room temperature and was evaporated in vacuo to remove the organic solvent. The residual aqueous layer was diluted with aqueous 2N NaOH solution (150 mL) then extracted with ethyl acetate (150 mL). The organic layer was separated off and washed with aqueous 2N NaOH solution (150 mL) followed by brine (150 mL). The organic layer was separated off, dried (MgSO$_4$) and concentrated in vacuo. The residue was triturated with diethyl ether. The solid was filtered in vacuo then dried to afford the title compound as a white solid (2.55 g, 58%). LC/MS: (PS-B5) R$_t$ 3.05 [M+H]$^+$ 414.18. $^1$H NMR (Me-d3-OD) 7.95 (2H, br s), 7.55 (2H, d), 7.48-7.41 (4H, m), 7.31 (2H, d), 3.87 (2H, q), 1.35 (9H, s).

1E. 2-Amino-1-(4-chloro-phenyl)-1-[4-(1H-pyrazol-4-yl)-phenyl]-ethanol (BOC deprotection step)

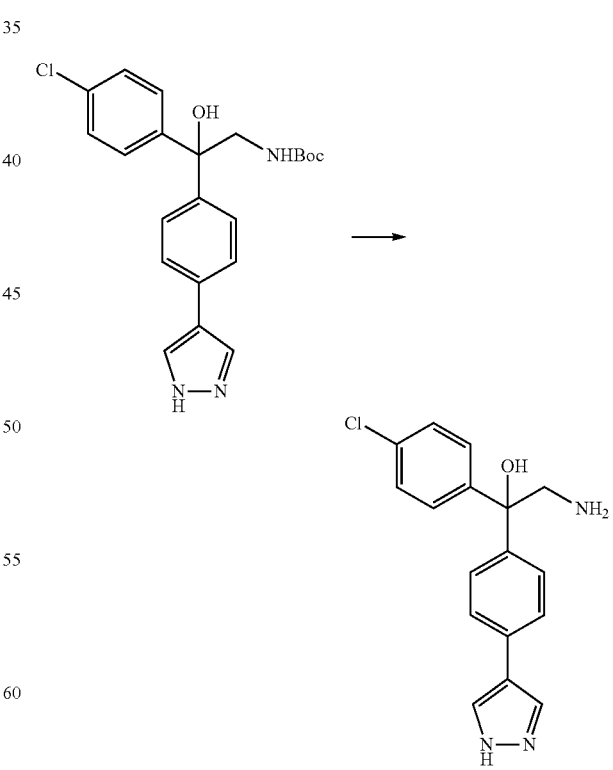

A suspension of the BOC amine (2.55 g, 6.16 mmol) in saturated HCl in Et$_2$O (50 ml) and methanol (50 ml) was stirred at room temperature for 20 hours. The reaction mixture was concentrated in vacuo and diluted with 2M NaOH (150 ml) and extracted with EtOAc (200 ml) (NB—prolonged shaking required to completely dissolve solid matter). The organic layer was washed with 1N HCl (100 ml). The aqueous layer was then separated and basified to pH12 with 2M NaOH. The desired product precipitates from solution and is then collected by vacuum filtration and dried for several days (1.89 g, 98%). $^1$H NMR (Me-d$_3$-OD) δ 3.29-3.38 (2H, m), 7.32 (2H, d), 7.41-7.46 (4H, m), 7.55 (2H, d), 7.94 (2H, s).

1F. Chiral Separation of Individual Enantiomers

Using the chiral LC methods described below, the compound (S)-2-amino-1-(4-chloro-phenyl)-1-[4-(1H-pyrazol-4-yl)-phenyl]-ethanol was separated from the R-enantiomer.
Chiral Analytical Conditions:
Eluent: MeOH+0.1% DEA at room Temperature
Flow: 0.7 ml/min
Total time: 25 min
Inj. Volume: 5 uL
Sample Conc: 1 mg/ml (in mobile phase)
Column: DAICEL Chiralpak AD-H; 250×4.6 mm
Wavelength: 230 or 257 nm
Chiral Preparative Conditions:
Eluent: MeOH+0.1% DEA at room Temperature
Flow: 13 ml/min
Total time: 29 min
Inj. Volume: 250 uL
Sample Conc: 100 mg/ml (in mobile phase)
Column: DAICEL Chiralpak AD-H; 250×20 mm
Wavelength: 230 or 257 nm The resulting (S)-2-amino-1-(4-chloro-phenyl)-1-[4-(1H-pyrazol-4-yl)-phenyl]-ethanol was characterised by polarimetry, chiral chromatography and crystallography.
Polarimetry The optical activities of both the S enantiomer and the R enantiomer were determined using an AA-10 automatic polarimeter (Optical Activity Limited).
S-Enantiomer 22.42 mg compound dissolved in 2 mls MeOH, Cell length=20 cm, Reading=+0.31, $[α]_D^{20}=+13.8°$ R-Enantiomer 20.14 mg dissolved in 10 mls MeOH (larger dilution due to bubble problems in the polarimeter cell), Reading=−0.03, Cell length=10 cm $[α]_D^{20}=−14.8°$ Chiral Chromatography Using the chiral analytical conditions described above and an injection volume of 5 μl), the S-enantiomer had a retention time of 15.283 minutes.
Crystallography Crystallographic analysis of the S-enantiomer in bPKA-PKB was carried out using the method described in Thomas G. Davies et al. "A Structural Comparison of Inhibitor Binding to PKB, PKA and PKA-PKB Chimera," *J. Mol. Biol.* 9 Jan. 2007: 17275837. The analysis indicated the presence of the S-enantiomer bound to protein.

Example 2

Alternative Synthesis of 2-Amino-1-(4-chloro-phenyl)-1-[4-iodo-phenyl]-ethanol

This example describes the preparation of 2-amino-1-(4-chloro-phenyl)-1-[4-iodo-phenyl]-ethanol, intermediate compound 1B in Example 1.

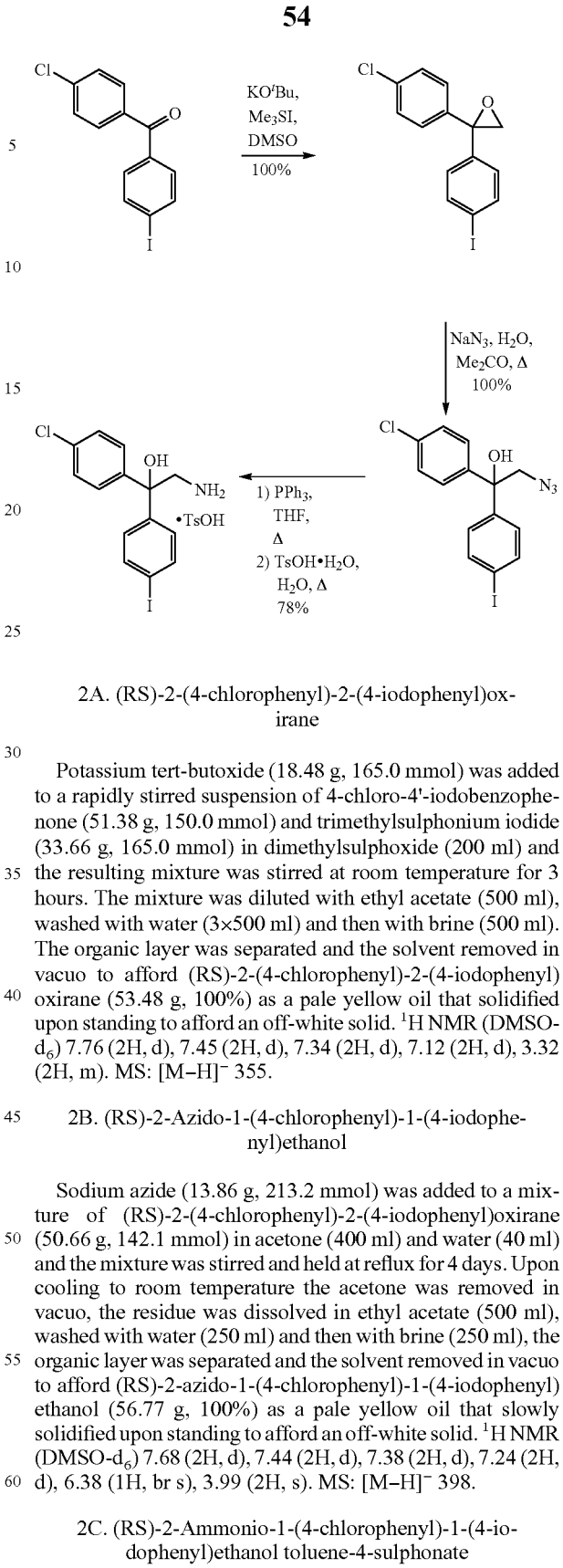

2A. (RS)-2-(4-chlorophenyl)-2-(4-iodophenyl)oxirane

Potassium tert-butoxide (18.48 g, 165.0 mmol) was added to a rapidly stirred suspension of 4-chloro-4'-iodobenzophenone (51.38 g, 150.0 mmol) and trimethylsulphonium iodide (33.66 g, 165.0 mmol) in dimethylsulphoxide (200 ml) and the resulting mixture was stirred at room temperature for 3 hours. The mixture was diluted with ethyl acetate (500 ml), washed with water (3×500 ml) and then with brine (500 ml). The organic layer was separated and the solvent removed in vacuo to afford (RS)-2-(4-chlorophenyl)-2-(4-iodophenyl) oxirane (53.48 g, 100%) as a pale yellow oil that solidified upon standing to afford an off-white solid. $^1$H NMR (DMSO-d$_6$) 7.76 (2H, d), 7.45 (2H, d), 7.34 (2H, d), 7.12 (2H, d), 3.32 (2H, m). MS: [M−H]$^-$ 355.

2B. (RS)-2-Azido-1-(4-chlorophenyl)-1-(4-iodophenyl)ethanol

Sodium azide (13.86 g, 213.2 mmol) was added to a mixture of (RS)-2-(4-chlorophenyl)-2-(4-iodophenyl)oxirane (50.66 g, 142.1 mmol) in acetone (400 ml) and water (40 ml) and the mixture was stirred and held at reflux for 4 days. Upon cooling to room temperature the acetone was removed in vacuo, the residue was dissolved in ethyl acetate (500 ml), washed with water (250 ml) and then with brine (250 ml), the organic layer was separated and the solvent removed in vacuo to afford (RS)-2-azido-1-(4-chlorophenyl)-1-(4-iodophenyl) ethanol (56.77 g, 100%) as a pale yellow oil that slowly solidified upon standing to afford an off-white solid. $^1$H NMR (DMSO-d$_6$) 7.68 (2H, d), 7.44 (2H, d), 7.38 (2H, d), 7.24 (2H, d), 6.38 (1H, br s), 3.99 (2H, s). MS: [M−H]$^-$ 398.

2C. (RS)-2-Ammonio-1-(4-chlorophenyl)-1-(4-iodophenyl)ethanol toluene-4-sulphonate Triphenylphosphine (31.44 g, 120.0 mmol) was added to a solution of (RS)-2-azido-1-(4-chlorophenyl)-1-(4-iodophenyl)ethanol (47.94 g, 120.0 mmol) in tetrahydrofuran (400 ml) and the mixture was stirred and held at reflux for 5 hours whereupon toluene-4-sulphonic acid monohydrate (22.8 g, 120.0 mmol) and water (40 ml) were added and the mixture was stirred and held at reflux for a further 16 hours. Upon cooling to room temperature the mixture was evaporated to dryness in vacuo. Ethyl acetate (600 ml) was added and the mixture was stirred rapidly at room temperature for 30 minutes to resuspend the solids. The solids were collected by suction filtration, rinsed with ethyl acetate (3×250 ml), sucked dry under reduced pressure and dried overnight at 50° C. in a vacuum oven to afford (RS)-2-ammonio-1-(4-chlorophenyl)-1-(4-iodophenyl)ethanol toluene-4-sulphonate (51.37 g, 78%) as a colourless solid. $^1$H NMR (DMSO-d$_6$) 7.73 (2H, d), 7.68 (3H, br s), 7.47 (4H, m), 7.43 (2H, d), 7.28 (2H, d), 7.12 (2H, d), 6.60 (1H, br s), 3.67 (2H, s), 2.30 (3H, s). MS: [M+H]$^+$ 374.

The product of Example 2C can be converted into the N-Boc derivative by the method of Example 1C (but using an additional equivalent of sodium hydroxide to take account of the toluene sulphonic acid salt) and then subjected to a Suzuki coupling reaction followed by removal of the Boc protecting group as described in Example 1D and Example 1E and the resulting mixture of enantiomers resolved by the method of Example 1F to give (S)-2-amino-1-(4-chloro-phenyl)-1-[4-(1H-pyrazol-4-yl)-phenyl]-ethanol.

Biological Activity

The biological activity of the compound of formula (I) is described in the following examples. In addition, the biological properties of the compound of formula (I) are described in the poster by John F. Lyons et al., page 3512s, Poster Session B, Abstract B251, AACR-NCI-EORTC International Conference: Molecular Targets and Cancer Therapeutics, Oct. 22-26, 2007, San Francisco, Calif. (copy available on the Astex Therapeutics website: www.astex-therapeutics.com or www.astex-therapeutics.com/investorsandmedia/publications)

Example 3

Measurement of PKA Kinase Inhibitory Activity (IC$_{50}$)

The compound of formula (I) can be tested for PK inhibitory activity using the PKA catalytic domain from Upstate Biotechnology (#14-440) and the 9 residue PKA specific peptide (GRTGRRNSI), also from Upstate Biotechnology (#12-257), as the substrate. A final concentration of 1 nM enzyme is used in a buffer that includes 20 mM MOPS pH 7.2, 40 µM ATP/γ$^{33}$P-ATP and 50 mM substrate. Compounds are added in dimethylsulphoxide (DMSO) solution to a final DMSO concentration of 2.5%. The reaction is allowed to proceed for 20 minutes before addition of excess orthophosphoric acid to quench activity. Unincorporated γ$^{33}$P-ATP is then separated from phosphorylated proteins on a Millipore MAPH filter plate. The plates are washed, scintillant is added and the plates are then subjected to counting on a Packard Topcount.

The % inhibition of the PKA activity is calculated and plotted in order to determine the concentration of test compound required to inhibit 50% of the PKA activity (IC$_{50}$).

Following the protocol described above, (S)-2-amino-1-(4-chloro-phenyl)-1-[4-(1H-pyrazol-4-yl)-phenyl]-ethanol was found to provide 44% inhibition of PKA at a concentration of 0.03 µM, whereas the IC$_{50}$ value of (R)-2-amino-1-(4-chloro-phenyl)-1-[4-(1H-pyrazol-4-yl)-phenyl]-ethanol was 0.25 µM. The results demonstrate that the S-enantiomer is significantly more potent than the R-enantiomer in the PKA assay.

Example 4

Measurement of PKB Kinase Inhibitory Activity (IC$_{50}$)

The inhibition of protein kinase B (PKB) activity by compounds can be determined essentially as described by Andjelkovic et al. (Mol. Cell. Biol. 19, 5061-5072 (1999)) but using a fusion protein described as PKB-PIF and described in full by Yang et al (Nature Structural Biology 9, 940-944 (2002)). The protein is purified and activated with PDK1 as described by Yang et al. The peptide AKTide-2T (H-A-R—K—R-E-R-T-Y—S—F-G-H—H-A-OH) obtained from Calbiochem (#123900) is used as a substrate. A final concentration of 0.6 nM enzyme is used in a buffer that includes 20 mM MOPS pH 7.2, 30 µM ATP/γ$^{33}$P-ATP and 25 µM substrate. Compounds are added in DMSO solution to a final DMSO concentration of 2.5%. The reaction is allowed to proceed for 20 minutes before addition of excess orthophosphoric acid to quench activity. The reaction mixture is transferred to a phosphocellulose filter plate where the peptide binds and the unused ATP is washed away. After washing, scintillant is added and the incorporated activity measured by scintillation counting.

The % inhibition of the PKB activity is calculated and plotted in order to determine the concentration of test compound required to inhibit 50% of the PKB activity (IC$_{50}$).

Following the protocol described above, the IC$_{50}$ value of (S)-2-amino-1-(4-chloro-phenyl)-1-[4-(1H-pyrazol-4-yl)-phenyl]-ethanol was found to be 0.01 µM, whereas the IC$_{50}$ value of (R)-2-amino-1-(4-chloro-phenyl)-1-[4-(1H-pyrazol-4-yl)-phenyl]-ethanol was 0.96 µM. The results demonstrate that the S-enantiomer is approximately 100 times as potent as the R-enantiomer in the PKB assay.

Example 5 hERG Activity

The activity of compound of formula (I) against the hERG K$^+$ ion channel can be determined using the assay described in the article by M. H. Bridgland-Taylor et al., *Journal of Pharmcaological and Toxicological Methods*, 54 (2006), 189-199.

Example 6

Determination of Potency against Cytochrome P450

The potency of the compound of Example 1 against cytochrome P450 (CYP450) enzymes 1A2, 2C9, 2C19, 3A4 and 2D6 was determined using the Pan Vera Vivid C450 screening kits available from Invitrogen (Paisley, UK). The CYP450s were supplied in the form of baculosomes containing the CYP450 and NADPH reductase and the substrates used were the fluorescent Vivid substrates. The final reaction mixtures were as follows:

1A2

100 mM potassium phosphate, pH 8, 1% acetonitrile, 2 µM 1A2 Blue vivid substrate, 100 µM NADP$^+$, 4 nM CYP450 1A2, 2.66 mM glucose-6-phosphate, 0.32 U/ml glucose-6-phosphate dehydrogenase.

2C9

50 mM potassium phosphate, pH 8, 1% acetonitrile, 2 μM Green vivid substrate, 100 μM NADP+, 8 nM CYP450 2C9, 2.66 mM glucose-6-phosphate, 0.32 U/ml glucose-6-phosphate dehydrogenase.

2C19

50 mM potassium phosphate, pH 8, 1% acetonitrile, 8 μM Blue vivid substrate, 100 μM NADP+, 4 nM CYP450 2C19, 2.66 mM glucose-6-phosphate, 0.32 U/ml glucose-6-phosphate dehydrogenase.

3A4

100 mM potassium phosphate, pH 8, 1% acetonitrile, 10 μM 3A4 Blue vivid substrate, 100 μM NADP+, 2.5 nM CYP450 3A4, 2.66 mM glucose-6-phosphate, 0.32 U/ml glucose-6-phosphate dehydrogenase.

2D6

100 mM potassium phosphate, pH 8, 1% acetonitrile, 5 μM 2D6 Blue vivid substrate, 100 μM NADP+, 16 nM CYP450 2D6, 2.66 mM glucose-6-phosphate, 0.32 U/ml glucose-6-phosphate dehydrogenase.

Fluorescence was monitored for 20 minutes at 30 second intervals on a Fluoroskan fluorescence plate reader. The excitation and emission wavelengths were 390 nm and 460 nm for 1A2, 2C19 and 3A4, 390 nm and 485 nm for 2D6 and 485 nm and 530 nm for 2C9. Initial rates were determined from progress curves.

The test compound was made up in acetonitrile and tested against the CYP450s at a concentration of 10 μM.

The compound of Example 1 had an $IC_{50}$ greater than 10 μM against 1A2, 2C9, 2C19, 3A4 and 2D6.

Example 7

Cell Based Phospho-Ser9 Gsk3β ELISA Assay Against pSer9 GSK3β

The effect on inhibiting PKB in U87MG cells is determined by the ability of compounds to inhibit phosphorylation of the direct downstream substrate GSK3β on serine 9. Cells are plated in 96 well plates and allowed to recover overnight prior to addition of the inhibitor compound for 1 hour. After 1 hour, cell are fixed and blocked with 3% paraformaldehyde, 0.25% gluteraldehyde, 0.25% Triton X100 and 5% Marvel in TBS-T. Following this cells are incubated with primary antibody directed to the phosphorylated form of GSK3β (Cell Signaling) overnight at 4° C. After washing, cells are incubated with secondary antibody using the DELFIA reagents (Eu—N1 anti-rabbit IgG antibody) for 1 h, and following enhancement plates are read on a time-resolved fluorescence reader at excitation 340 nm and emission 640 nm. All cells are obtained from ECACC (European Collection of Cell Cultures).

Protocol

1. U87MG cells plated at 12,500 cells/well in 160 ul media/well in a 96 well plate
2. Incubate for 24 hours at 37° C.
3. Treat cells with the inhibitor and DMSO control
4. Incubate for 1 hour at 37° C.
5. Media flicked from the plate and blot on paper
6. 100 μl fixing solution added to each well (3% paraformaldehyde, 0.25% gluteraldehyde, 0.25% Triton X100)
7. Incubate for 30 minutes at 37° C.
8. Wash 1× with water/0.1% Tween20
9. Block with 100 μl 5% milk/TBS-T
10. Incubate for 30 minutes at 37° C.
11. 100 μl primary antibody diluted in 5% milk/TBS-T added to each well (CST #9336 Phospho-Ser9 GSK3β antibody used at 1:250)
   include a column control with no 1 ab—just 5% milk/TBS-T
   can also include a column of Zymed rabbit IgG (02-6102-5 mg/mL) control diluted in 5% milk/TBS-T to the same concentration as the phospho-Ser9 GSK3β if required
12. Incubate overnight at 4° C.
13. Wash 3× with water/0.1% Tween20
14. 100 μl secondary antibody diluted in Delfia Assay Buffer added to each well (Delfia Eu—N1 anti-rabbit IgG antibody used at 0.30 μg/ml final conc)
15. Incubate for 1 hour at 37° C.
16. Wash 3× with water/0.1% Tween20
17. 100 μl Delfia Enhancement Solution added to each well
18. Shake on plate shaker for 15 minutes
19. Read on Delfia programme (excitation 340 nm–emission 640 nm)=Europium counts
20. Wash 1× with water/0.1% Tween 20
21. 200 μl BCA solution added per well (BCA with 1:50 Copper II Sulfate)
22. Incubate for 30 minutes at 37° C.
23. Read at absorbance 562 nm=protein concentration The compound (S)-2-amino-1-(4-chloro-phenyl)-1-[4-(1H-pyrazol-4-yl)-phenyl]-ethanol was found to have an $IC_{50}$ of 1.1 μM in the above mechanistic assay, whereas the $IC_{50}$ value of (R)-2-amino-1-(4-chloro-phenyl)-1-[4-(1H-pyrazol-4-yl)-phenyl]-ethanol was >50 μM, i.e. the R-enantiomer was essentially inactive.

Example 8

ROCK-II (h) Assay Protocol

The compound (S)-2-amino-1-(4-chloro-phenyl)-1-[4-(1H-pyrazol-4-yl)-phenyl]-ethanol was tested in the ROCK-II assay set out below.

In a final reaction volume of 25 μl ROCK-II (h) (5-10 mU) is incubated with 50 mM Tris pH 7.5, 0.1 mM EGTA, 30 μM KEAKEKRQEQIAKRRRLSSLRASTSKSGGSQK, 10 mM MgAcetate and [γ-$^{33}$P-ATP] (specific activity approx. 500 cpm/pmol, concentration as required). The reaction is initiated by the addition of the MgATP mix. After incubation for 40 minutes at room temperature, the reaction is stopped by the addition of 5 μl of a 3% phosphoric acid solution. 10 μl of the reaction is then spotted onto a P30 filtermat and washed three times for 5 minutes in 75 mM phosphoric acid and once in methanol prior to drying and scintillation counting.

In the assay, (S)-2-amino-1-(4-chloro-phenyl)-1-[4-(1H-pyrazol-4-yl)-phenyl]-ethanol was found to have an $IC_{50}$ of less than 10 nM in the above assay, i.e. below the limit of the assay.

Example 9 p70S6K Radiometric Assay

The compound (S)-2-amino-1-(4-chloro-phenyl)-1-[4-(1H-pyrazol-4-yl)-phenyl]-ethanol was tested in the p70S6K radiometric assay described below.

Overview

P70S6 enzyme is bought from Upstate and used at 2 nM in the assay.

The substrate S6 cocktail (AKRRRLSSLRA) is used at 25 μm (Km has not been determined). In the phosphoryl transfer reaction, the $^{33}$P-γ phosphate from ATP is transferred to the serine residue. The reaction mixture is transferred to a phosphocellulose filter plate where the peptide binds and the unused ATP is washed away. After washing, scintillant is added and the incorporated activity measured by scintillation counting.

Reagents
P70S6 kinase (T412E) active from Upstate (#14-486)
S6 kinase substrate cocktail from Upstate (#20-122)
Assay Buffer 10 mM MOPS pH 7.0
    0.1 mg/ml BSA
    0.001% Brij-35
    0.5% glycerol
    0.2 mM EDTA
    10 mM $MgCl_2$
    0.01% β-mercaptoethanol
    Made as a 10× stock, stored at 20° C. in 2 ml aliquots
    15 μM ATP
    ATP (10 mM stock) added fresh from concentrated stocks. ATP will break down over time, keep on ice as far as possible and use small aliquots to ensure the stock is fresh.
$\gamma^{33}$P-ATP APBiotech (BF1000)
12.5% orthophosphoric acid
0.5% orthophosphoric acid
Microscint 20 (Packard)
Assay Preparation
Enzyme mix (per 1 ml—100 assay points):
743.75 μl H20
250 μl 10× assay buffer
3.75 μl 10 mM ATP
2.5 μl enzyme
Substrate mix (per 1 ml—100 assay points):
250 μl S6 cocktail substrate
750 μl H20
3.5 μl $^{33}$P-ATP (BF1000 from APBiotech)
    The amount of $^{33}$P-ATP added assumes it is on its reference date. The exact amount needs to be adjusted with time.
    Compounds—prepare a dilution curve in DMSO in a polypropylene 96 well plate to 40× final assay concentration (final DMSO 2.5%).
    Dilute 1:8 in water (adding 5 μl of compound to 35 μl water is sufficient).
Assay Setup
In a polypropylene 96 well plate add in order:
    5 μl compound
    10 μl substrate mix
    10 μl enzyme mix
    Final ATP concentration is approximately 15 μM. KM for ATP calculated to 47 uM radiometrically. Controls are "no compound" (DMSO only) and "no enzyme" (use 10 μl of the enzyme mix prior to adding enzyme). Cover with a plate seal (TopSeal A—Packard) or plastic lid from filter plate (moderate radiation barrier). Mix by gentle shaking. Incubate at room temperature for 50 minutes. Stop the reaction by adding 20 μl of 2% orthophosphoric acid.
Filtration Step
    Pre-wet the wells of a Millipore MAPH NOB plate with 50 μl of 0.5% orthophosphoric acid wash buffer. Filter the liquid through on a Millipore vacuum filtration unit. Transfer the whole of the stopped reaction to the wells. Filter through. Wash twice with 200 μl of 0.5% orthophosphoric acid wash buffer. Vacuum to near dryness. Remove the plate support and allow to the filters to dry further on tissue paper. Snap the plate into an adapter for the Packard TopCount. Add 20 μl of Microscint 20 scintillant, seal with a sheet of Topseal A and count for 30 s on the TopCount.

In the assay, (S)-2-amino-1-(4-chloro-phenyl)-1-[4-(1H-pyrazol-4-yl)-phenyl]-ethanol was found to have an $IC_{50}$ of 12 nM.

Pharmaceutical Formulations

Example 10 i) Tablet Formulation

A tablet composition containing a composition as defined herein is prepared by mixing 50 mg of the compound with 197 mg of lactose (BP) as diluent, and 3 mg magnesium stearate as a lubricant and compressing to form a tablet in known manner.

(ii) Capsule Formulation

A capsule formulation is prepared by mixing 100 mg of a composition as defined herein with 100 mg lactose and filling the resulting mixture into standard opaque hard gelatin capsules.

(iii) Injectable Formulation I

A parenteral composition for administration by injection can be prepared by dissolving a composition as defined herein (e.g. in a salt form) in water containing 10% propylene glycol to give a concentration of active compound of 1.5% by weight. The solution is then sterilised by filtration, filled into an ampoule and sealed.

(iv) Injectable Formulation II

A parenteral composition for injection is prepared by dissolving in water a composition as defined herein (e.g. in salt form) (2 mg/ml) and mannitol (50 mg/ml), sterile filtering the solution and filling into sealable 1 ml vials or ampoules.

v) Injectable formulation III

A formulation for i.v. delivery by injection or infusion can be prepared by dissolving the compound of formula (I) (e.g. in a salt form) in water at 20 mg/ml. The vial is then sealed and sterilised by autoclaving.

vi) Injectable formulation IV

A formulation for i.v. delivery by injection or infusion can be prepared by dissolving the compound of formula (I) (e.g. in a salt form) in water containing a buffer (e.g. 0.2 M acetate pH 4.6) at 20 mg/ml. The vial is then sealed and sterilised by autoclaving.

(vii) Subcutaneous Injection Formulation

A composition for sub-cutaneous administration is prepared by mixing a composition as defined herein with pharmaceutical grade corn oil to give a concentration of 5 mg/ml. The composition is sterilised and filled into a suitable container.

viii) Lyophilised Formulation

Aliquots of formulated compound of formula (I) are put into 50 ml vials and lyophilized. During lyophilisation, the compositions are frozen using a one-step freezing protocol at (−45° C.). The temperature is raised to −10° C. for annealing, then lowered to freezing at −45° C., followed by primary drying at +25° C. for approximately 3400 minutes, followed by a secondary drying with increased steps if temperature to 50° C. The pressure during primary and secondary drying is set at 80 millitor.

EQUIVALENTS

The foregoing examples are presented for the purpose of illustrating the invention and should not be construed as imposing any limitation on the scope of the invention. It will readily be apparent that numerous modifications and alterations may be made to the specific embodiments of the invention described above and illustrated in the examples without departing from the principles underlying the invention. All such modifications and alterations are intended to be embraced by this application.

The invention claimed is:

1. A method of modulating a cellular process by inhibiting the activity of a ROCK kinase comprising administering a therapeutically effective amount of a composition comprising (S)2-amino-1-(4-chloro-phenyl)-1-[4-(1H-pyrazol-4-yl)-phenyl]-ethanol in the form of a hydrochloride salt, wherein at least 98% of 2-amino-1-(4-chloro-phenyl)-1-[4-(1H-pyrazol-4-yl)-phenyl]-ethanol hydrochloride salt in the composition is in the S-enantiomeric form.

2. A method for inhibiting ROCK kinase; which method comprises bringing the ROCK kinase in a cellular environment, into contact with a composition comprising (S)2-amino-1-(4-chloro-phenyl)-1-[4-(1H-pyrazol-4-yl)-phenyl]-ethanol in the form of a hydrochloride salt, wherein at least 98% of 2-amino-1-(4-chloro-phenyl)-1-[4-(1H-pyrazol-4-yl)-phenyl]-ethanol hydrochloride salt in the composition is in the S-enantiomeric form.

3. A method according to claim 1 wherein the (S)2-amino-1-(4-chloro-phenyl)-1-[4-(1H-pyrazol-4-yl)-phenyl]-ethanol is in the form of a di-hydrochloride salt.

4. A method according to claim 2 wherein the (S)2-amino-1-(4-chloro-phenyl)-1-[4-(1H-pyrazol-4-yl)-phenyl]-ethanol is in the form of a di-hydrochloride salt.

5. A method according to claim 1 wherein at least 99% of 2-amino-1-(4-chloro-phenyl)-1-[4-(1H-pyrazol-4-yl)-phenyl]-ethanol hydrochloride salt in the composition is in the S-enantiomeric form.

6. A method according to claim 2 wherein at least 99% of 2-amino-1-(4-chloro-phenyl)-1-[4-(1H-pyrazol-4-yl)-phenyl]-ethanol hydrochloride salt in the composition is in the S-enantiomeric form.

7. A method according to claim 3 wherein at least 99% of 2-amino-1-(4-chloro-phenyl)-1-[4-(1H-pyrazol-4-yl)-phenyl]-ethanol di-hydrochloride salt in the composition is in the S-enantiomeric form.

8. A method according to claim 4 wherein at least 99% of 2-amino-1-(4-chloro-phenyl)-1-[4-(1H-pyrazol-4-yl)-phenyl]-ethanol di-hydrochloride salt in the composition is in the S-enantiomeric form.

\* \* \* \* \*